(12) United States Patent
Balsamo et al.

(10) Patent No.: US 6,242,433 B1
(45) Date of Patent: Jun. 5, 2001

(54) GERANYLGERANYL-DERIVATIVES, PROCESS FOR THE PREPARATION THEREOF AND RELATED PHARMACEUTICAL COMPOSITIONS

(75) Inventors: Aldo Balsamo, Lucca; Bruno Macchia; Marco Macchia, both of Livorno; Massimo Baldacci, Pisa; Romano Danesi, Livorno; Mario Del Tacca, Pisa, all of (IT)

(73) Assignee: Laboratori Baldacci SpA, Pisa (IT)

( * ) Notice: Subject to any disclaimer, the term of this patent is extended or adjusted under 35 U.S.C. 154(b) by 0 days.

(21) Appl. No.: 09/077,196

(22) PCT Filed: Nov. 21, 1996

(86) PCT No.: PCT/EP96/05202

§ 371 Date: Sep. 15, 1998

§ 102(e) Date: Sep. 15, 1998

(87) PCT Pub. No.: WO97/19091

PCT Pub. Date: May 29, 1997

(30) Foreign Application Priority Data

Nov. 23, 1995 (IT) .............................................. MI95A2431

(51) Int. Cl.[7] ...................... A61K 31/664; A61K 31/662; A61K 31/661; C07F 9/38; C07F 9/40; C07F 9/22; C07F 9/24

(52) U.S. Cl. .......................... 514/108; 514/114; 514/119; 514/129; 514/134; 558/173; 562/8; 562/15; 562/21; 562/23

(58) Field of Search ..................................... 514/108, 114, 514/119, 129, 134; 558/173; 562/8, 15, 21, 23

(56) References Cited

U.S. PATENT DOCUMENTS

| 5,254,715 |   | 10/1993 | Picard et al. . |
|---|---|---|---|
| 5,510,510 | * | 4/1996 | Patel et al. .......................... 562/23 X |
| 5,574,025 | * | 11/1996 | Anthony et al. ...................... 514/129 |

FOREIGN PATENT DOCUMENTS

| 0 356 866 | 3/1990 | (EP) . |
|---|---|---|
| 0 534 546 | 3/1993 | (EP) . |
| 0 609 440 | 8/1994 | (EP) . |
| 2 294 462 | 5/1996 | (GB) . |
| WO 94 19357A | 9/1994 | (WO) . |

\* cited by examiner

*Primary Examiner*—Michael G. Ambrose
(74) *Attorney, Agent, or Firm*—Nixon & Vanderhye

(57) ABSTRACT

The present invention relates to novel geranylgeranyl derivatives and the pharmaceutically acceptable salts thereof having antiproliferative activity in eukaryotic cells with respect to the inhibition of protein geranygeranylation. The invention also relates to the pharmaceutical compositions containing the novel derivatives and to the process of preparation thereof.

29 Claims, No Drawings

GERANYLGERANYL-DERIVATIVES, PROCESS FOR THE PREPARATION THEREOF AND RELATED PHARMACEUTICAL COMPOSITIONS

The present invention relates to novel geranylgeranyl-derivatives and their pharmaceutically acceptable salts having inhibiting activity with respect to protein geranylgeranylation in eukaryotic cells.

It is known in biology that proteins bearing the aminoacidic sequence CysAAX (that is to say a cysteine molecule which is linked to two aliphatic aminoacids AA, linked to each other and, on their turn, linked to any aminoacid X) on their carboxy end group are subjected to a number of post-translational modifications in eukaryotic cells.

Said modifications consist in the formation of a covalent bond between the cysteinic residue of the protein and an isoprenoid lipid, followed by the proteolysis of the three terminal aminoacids AAX and by the α-carboxy-methyl esterification of the isoprenyl-cystein (Giannakouros T., Magee A. I., *Lipid' modifications of proteins* (Schlesinger M J, ed.), CRC Press, Boca Raton, 1993; 136–162). The isoprenoid lipid can be farnesyl (15 carbon atoms) or geranylgeranyl (20 carbon atoms) and the isoprenylation is necessary for the acquisition of the biological properties of the protein itself (Grünler J., Ericsson J., Dallner G., *Biochim. Biophys. Acta*, 1994; 1212, 259–277). A typical example of a farnesylated protein is the p21ras, while the low-molecular weight proteins of the ras superfamily among which p21rho, p21rap1, p21rac and cdc42, are geranylgeranylated.

The proteins isoprenylation enzymology has been the object of an intense research and the following enzymes which catalyze the most important steps of the biochemical way leading to the formation of isoprenoid compounds have been characterized (Grünler J., Ericsson J., Dallner G., *Biochim. Biophys. Acta*, 1994; 1212, 259–277):

3-hydroxy-3-methylglutaryl coenzyme A reductase;

farnesyl diphosphate synthetase;

protein:farnesyl transferase;

geranylgeranyl diphosphate synthetase;

protein:geranylgeranyl transferase type I;

protein:geranylgeranyl transferase type II.

The 3-hydroxy-3-methylglutaryl coenzyme A reductase is the enzyme responsible for the synthesis of mevalonic acid from which originate, as a result of the activity of farnesyl diphosphate synthetase and geranylgeranyl diphosphate synthetase, both farnesyl diphosphate (farnesyl-FF) and geranylgeranyl diphosphate (geranylgeranyl-FF) which are the two isoprenoids used for protein isoprenylation. On the contrary the protein:farnesyl transferase and the protein:geranylgeranyl transferases (type I and II) catalyze the transfer of the group farnesyl and geranylgeranyl, respectively, to proteins.

It has been recently demonstrated the fundamental part played by geranylgeranylated proteins, among which specifically p21rho, p21rap1, rac and cdc42, in eukaryotic cells cell proliferation, where they control essential functions as the actin organization of cytoskeleton and of intercellular adhesion plaques (Olson M. F., Ashworth A., Hall A., *Science* 1995; 269; 1270–1272). The above discovery is of great importance as regards the possible implications in the therapy of pathologies characterized by an excessive cell proliferation.

The object of the present invention are the novel compounds having general formula:

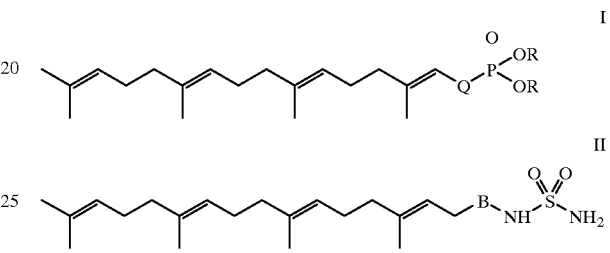

wherein:

Q=

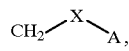

$CH_2$—$CH_2$, CHOH

X=ONH, ONHCO, $OCH_2CO$, $OCH_2P(O)OH$, $CH_2P(O)OH$, NHCO, $NCH_3CO$, $OSO_2$, $NHSO_2$;

A=R'CR'', CHR'''$CH_2$, NH when X=$OSO_2$, $NHSO_2$;

B=OCO, O, ONHCO, NHCO, $NCH_3CO$;

R=H, $CH_3$, $CH_2CH_3$;

R'=H, $CH_3$, $CH_2CH_3$;

R''=H, $CH_3$, $CH_2CH_3$;

R'''=H, COOH;

and pharmaceutically acceptable salts thereof, with acids and bases, organic and inorganic, having inhibiting activity with respect to protein geranylgeranylation in eukaryotic cells.

Preferred compounds within the scope of the invention are the following:

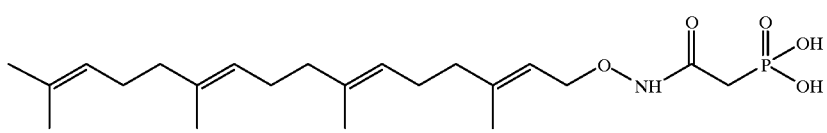

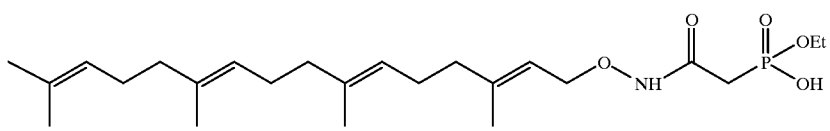

-continued
3)
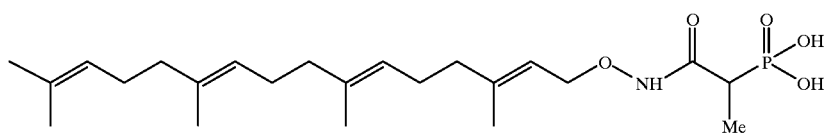
4)
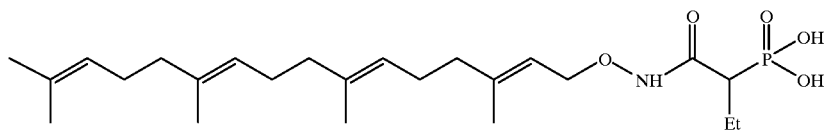
5)
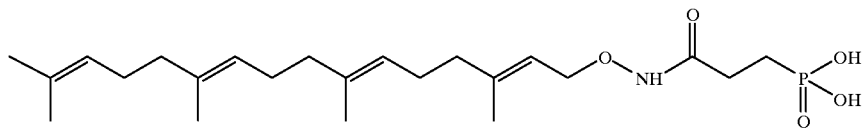
6)
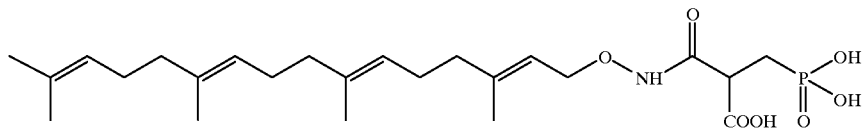
7)
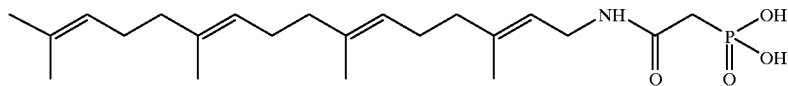
8)
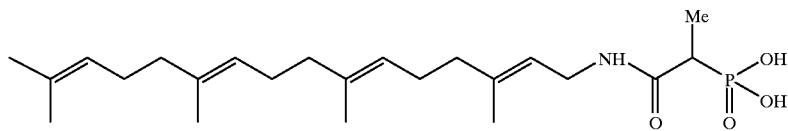
9)
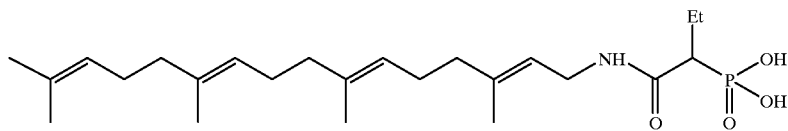
10)
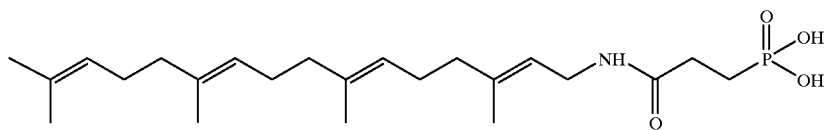
11)
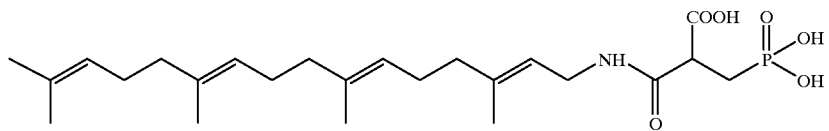
12)
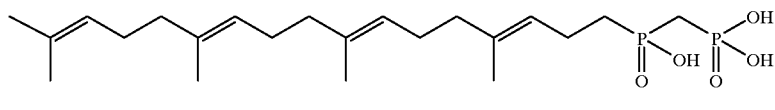
13)
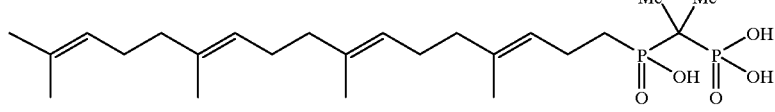

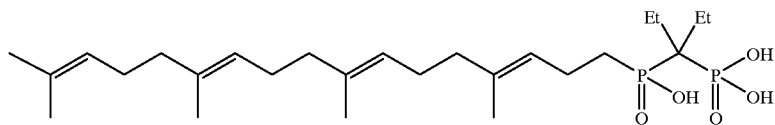

14)

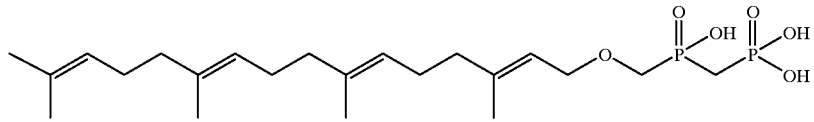

15)

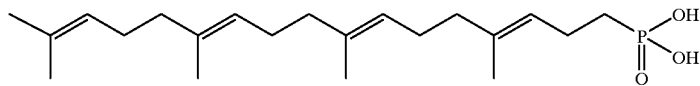

16)

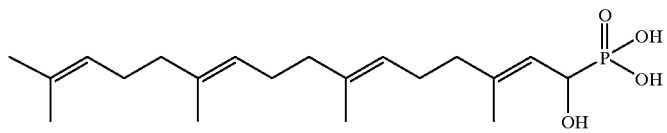

17)

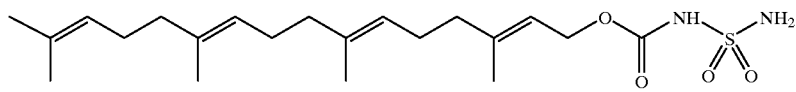

18)

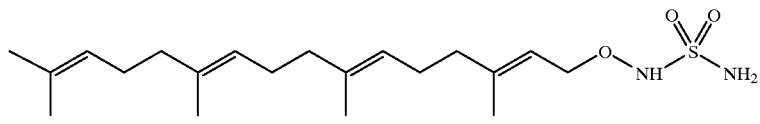

19)

It has been in fact surprisingly found that the compounds according to the present invention can prevent the post-translational geranylgeranylation and, as a consequence, the biological function of cellular proteins which perform essential functions in cellular replication mechanism. Said compounds can therefore be useful in the treatment of pathologies characterized by an excessive cell proliferation, among which are benign and malignant tumors, vascular and renal diseases on a degenerative-proliferative basis, as for example atherosclerosis and glomerulonephritis.

The ability of the compounds according to the present invention of inhibiting the protein geranylgeranylation has been evaluated by means of an in vitro test on a malignant tumoral human cell line which has been treated with the following geranylgeranyl-derivatives:

- dipotassium salt of (E,E,E)-{2-oxo-2-[[(3,7,11,15-tetramethyl-2,6,10,14-hexadecatetraenyl)oxy]amino]ethyl}phosphonic acid (reported on Table 1 with the abbreviation BAL9504) whose preparation is disclosed in example 1;
- monosodium salt of the monoethyl-ester of (E,E,E)-{2-oxo-2[[(3,7,11,15-tetramethyl-2,6,10,14-hexadecatetraenyl)oxy]amino]ethyl}phosphonic acid (reported on Table 1 with the abbreviation BAL9505) whose preparation is disclosed in example 2;
- dipotassium salt of (E,E,E)-{3-oxo-3-[[(3,7,11,15-tetramethyl-2,6,10,14-hexadecatetraenyl)oxy]amino]propyl}phosphonic acid (reported on Table 1 with the abbreviation BAL9603) whose preparation is disclosed in example 5;
- dipotassium salt of (E,E,E)-[2-oxo-2-[(3,7,11,15-tetramethyl-2,6,10,14-hexadecatetraenyl)amino]ethyl] phosphonic acid (reported on Table 1 with the abbreviation BAL9605) whose preparation is disclosed in example 7;
- dipotassium salt of (E,E,E)-[3-oxo-3-[(3,7,11,15-tetramethyl-2,6,10,14-hexadecatetraenyl)amino]propyl]phosphonic acid (reported on Table 1 with the abbreviation BAL9608) whose preparation is disclosed in example 10;
- tripotassium salt of (E,E,E)-[[(4,8,12,16-tetramethyl-3,7,11,15-heptadecatetraenyl)hydroxyphosphoryl]methyl] phosphonic acid (reported on Table 1 with the abbreviation BAL9609) whose preparation is disclosed in example 12;
- tripotassium salt of (E,E,E)-1-methyl-1[(4,8,12,16-tetramethyl-3,7,11,15-heptadecatetraenyl)hydroxyphosphoryl]ethylphosphonic acid (reported on Table 1 with the abbreviation BAL9610) whose preparation is disclosed in example 13;
- tripotassium salt of (E,E,E)-1-ethyl-1-[(4,8,12,16-tetramethyl-3,7,11,15-heptadecatetraenyl)hydroxyphosphoryl]propylphosphonic acid (reported on Table 1 with the abbreviation BAL9611) whose preparation is disclosed in example 14;
- dipotassium salt of (E,E,E)-(4,8,12,16-tetramethyl-3,7,11,15-heptadecatetraenyl)phosphonic acid (reported on Table 1 with the abbreviation BAL9613) whose preparation is disclosed in example 16;
- (E,E,E)-O-(3,7,11,15-tetramethyl-2,6,10,14-hexadecatetraenyl)-N-(aminosulfonyl)urethane (reported on Table 1 with the abbreviation BAL9503) whose preparation is disclosed in example 18;

(E,E,E)-1-[(aminosulfonyl)aminoxy]-3,7,11,15-tetramethyl-2,6,10,14-hexadecatetraene (reported on Table 1 with the abbreviation BAL9614) whose preparation is disclosed in example 19.

The cells have been treated with increasing amounts of the geranylgeranyl derivatives BAL9504, BAL9505, BAL9603, BAL9605, BAL9608, BAL9609, BAL9610, BAL9611, BAL9613, BAL9503, BAL9614, (1–75 $\mu$M) and, after 24 hours, they have been collected and solubilized in a lysis solution containing non-ionic detergents. The soluble fraction has been collected by centrifugation and proteins separated by means of acrylamide gel electrophoresis and subsequently transferred onto a polyvinylidene fluoride (PVDF) membrane.

The presence of the geranylgeranylated protein p21rap1 has been then evidenced by means of a specific polyclonal antibody followed by chemiluminescent detection by means of a secondary antibody linked to alkaline phosphatase as previously described (M. A. Mansfield, *FASEB J., S*, A1428, 1994). The presence of the protein under examination has been demonstrated by the appearance of a band in the radiographic film. The inhibition of p21rap1 geranylgeranylation achieved by means of the treatment with the compounds of the present invention has been demonstrated by the progressive increase of a band having a slower electrophoretic mobility than the one of the isoprenylated mature protein, indicating the presence of an immature non-geranylgeranylated protein (following the method described by R. Danesi et. al., *Mol. Pharmacol.*, 47, 1106, 1995). At the higher concentration (75 $\mu$M) the amount of the non-isoprenylated protein was equal to that of the isoprenylated one, in particular as regards to compounds BAL9503, BAL9504 and BAL9505.

The relevance of such an effect on cell proliferation has been then evaluated by studying the citotoxicity of the above-mentioned compounds on the of human pancreas cancer MIA PaCa-2 cell line following the method described by R. Danesi et. al., *Mol. Pharmacol.*, 47, 1106, 1995.

The results of this research are shown in Table 1 where the $IC_{50}$ values (the concentration that produces 50% reduction in cell growth) are reported; these results demonstrate that increasing the concentration of the geranylgeranyl derivatives causes a progressive decrease in the cellular survival, corresponding to a citotoxicity increases of the same on the MIA PaCa-2 cell line.

TABLE I

| Compound | Example | $IC_{50}$ ($\mu$M) |
|---|---|---|
| BAL9504 | 1 | 2.1 |
| BAL9505 | 2 | >30 |
| BAL9603 | 5 | >30 |
| BAL9605 | 7 | 7.7 |
| BAL9608 | 10 | 16.7 |
| BAL9609 | 12 | 3.5 |
| BAL9610 | 13 | >30 |
| BAL9611 | 14 | 1.5 |
| BAL9613 | 16 | >30 |
| BAL9503 | 18 | 10.5 |
| BAL9614 | 19 | 11.9 |

In confirmation on what above-reported, it is possible to observe that the geranylgeranyl derivatives (in particular BAL9504, BAL9605, BAL9609, BAL9611 and BAL9503) also induce death for apoptosis in the MIA PaCa-2 cell line treated at 1–75 $\mu$M with respect to the non-treated cells used for comparison. Apoptosis consists in enzymatic digestion of nuclear DNA by endogenous nucleases within the cell and it occurs when cell replication is impaired by agents that block cell cycle progression towards mitosis. The data of this experiment show that treatment with the geranylgeranyl derivatives induced up to ten-fold increase in the amount of fragmented, apoptotic DNA, as evaluated by means of an enzyme-linked immunosorbent assay (ELISA) technique with photometric lecture of the enzymatically-digested DNA recovered from MIA PaCa-2 cells (following the method described by R. Danesi et. al., *Mol. Pharmacol.*, 47, 1106, 1995).

The citotoxicity of the geranylgeranyl-derivatives BAL9504 and BAL9503 has also been evaluated on the normal diploid fibroblast cells MRC-5 from human lung following the method described by R. Danesi et. al., *Mol. Pharmacol.*, 47, 1106, 1995. Table 2 reports the concentration of the compounds under study that produces 50% growth inhibition ($IC_{50}$) in MRC-5 and MIA PaCa-2 cell lines together with the sensibility index, that is the ratio between the $IC_{50}$ in MRC-5 and MIA PaCa-2 cells.

From the data reported in the Table it is possible to underline a good action selectivity of the products, as the tumoral cells are more sensitive than the normal ones to the citotoxic effect of the geranylgeranyl-derivatives. Such a behavior cannot be simply explained on the basis of the different cellular replication rate between MRC-5 and MIA PaCa-2 cells as the MRC-5 fibroblasts are cells in active mitosis.

TABLE 2

| Compound | Cellular line | $IC_{50}$ | Sensibility Index |
|---|---|---|---|
| BAL9504 | MRC-5 | 54.6$\mu$M | 26 |
|  | MIA PaCa-2 | 2.1$\mu$M |  |
| BAL9503 | MRC 5 | 256.3$\mu$M | 24.4 |
|  | MIA PaCa-2 | 10.5$\mu$M |  |

The compounds of the present invention can be prepared by methods which result in a C-alkylation or O-alkylation or O-acylation of the hydroxymethyl group of all trans geranylgeraniol according to the steps here-below reported:

by means of conversion of trans geranylgeraniol into the corresponding oxyamine or amine derivatives and subsequent condensation with the appropriate reactants to give the corresponding phosphonic ester intermediates which are then hydrolized to yield final product having general formula:

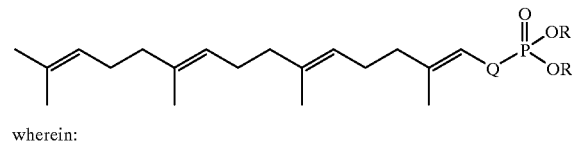

wherein:

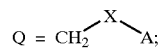

X=ONH, ONHCO, OCH$_2$CO, NHCO, NCH$_3$CO, NHSO$_2$;

A=R'CR'', CHR'''CH$_2$, NH when NHSO$_2$;

R=H, CH$_3$, CH$_2$CH$_3$;

R'=H, CH$_3$, CH$_2$CH$_3$;

R''=H, CH$_3$, CH$_2$CH$_3$;

R'''=H, COOH;

(see for example preparation of compounds 1, 2, 3, 4, 5, 6, 7, 8, 9, 10, 11);

by means of condensation of trans geranylgeranylbromide with the appropriate reactants to give the corresponding phosphonic ester intermediates which are then hydrolized to yield the final product having general formula:

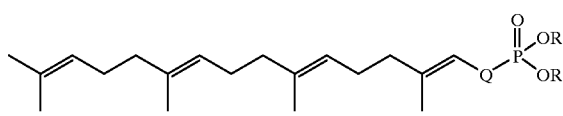

wherein:

Q=

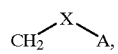

CH$_2$—CH$_2$;
X=CH$_2$P(O)OH;
A=R'CR", CHR'''CH$_2$;
R=H, CH$_3$, CH$_2$CH$_3$;
R'=H, CH$_3$, CH$_2$CH$_3$;
R"=H, CH$_3$, CH$_2$CH$_3$;
R'''=H, COOH;
(see for example preparation of compounds 12, 13, 14, 16);

by means of condensation of trans geranylgeraniol with the appropriate reactants to give the corresponding phosphonic ester intermediates which are partially hydrolized, further condensed with the appropriate reactants and then fully hydrolized to yield final product having general formula:

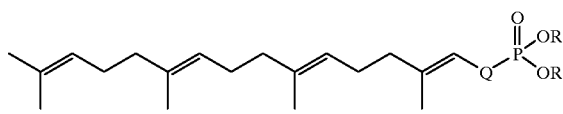

wherein:

Q=

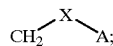

X=OCH$_2$P(O)OR;
A=R'CR", CHR'''CH$_2$;
R=H, CH$_3$, CH$_2$CH$_3$;
R'=H, CH$_3$, CH$_2$CH$_3$;
R"=H, CH$_3$, CH$_2$CH$_3$;
R'''=H, COOH;
(see for example preparation of compound 15);

by means of condensation of trans geranylgeranial or trans geranylgeraniol with the appropriate reactants to give the corresponding phosphonic ester intermediates which are then hydrolized to yield the final products having general formula:

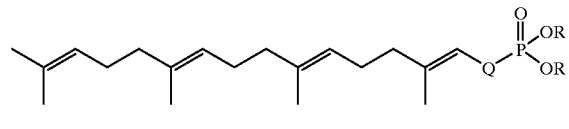

wherein:

Q=

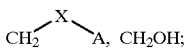, CH$_2$OH;

X=OSO$_2$;
A=NH;
R=H, CH$_3$, CH$_2$CH$_3$;
(see for example preparation of compound 17);

by means of condensation of trans geranylgeraniol or its oxyamine derivative with the appropriate reactants to yield the final products having general formula:

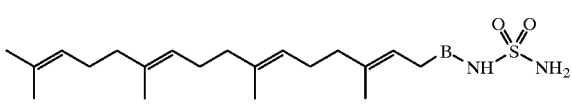

wherein:

B=OCO, O, ONHCO, NHCO, NCH$_3$CO;
(see for example preparation of compounds 18 and 19).

A second object of the present invention is therefore represented by the processes for the preparation of compounds having general formula I and II. A third object of the present invention is also represented by the novel intermediates having general formula:

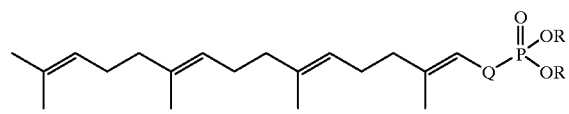

wherein:

Q=

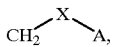

CH$_2$—CH$_2$, CHOH
X=ONH, ONHCO, OCH$_2$CO, OCH$_2$P(O)OR, CH$_2$P(O)OR, NHCO, NCH$_3$CO;
A=R'CR", CHR'''CH$_2$, NH when X=OSO$_2$, NHSO$_2$;
B=OCO, O, ONHCO, NHCO, NCH$_3$CO;
R=CH$_3$, CH$_2$CH$_3$;
R'=H, CH$_3$, CH$_2$CH$_3$;
R"=H, CH$_3$, CH$_2$CH$_3$;
R'''=H, COOEt, COOMe;

or having general formula:

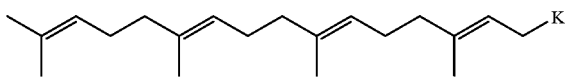

wherein:

K=NH$_2$, ONH$_2$
used for the preparation of the compounds according to the present invention.

A further object is then represented by the pharmaceutical compositions containing the novel compounds of the present invention.

The following examples illustrate the invention without anyhow limiting it.

EXAMPLE 1

Synthesis of the Dipotassium Salt of (E,E,E)-{2-Oxo-2-[[(3,7,11,15-Tetramethyl-2,6,10,14-Hexadecatetraenyl)Oxy]Amino]Ethyl}Phosphonic Acid

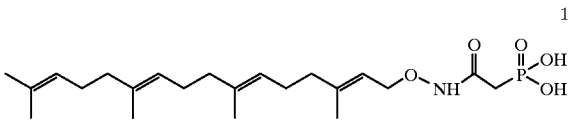

Compound 1 was prepared as shown in SCHEME 1

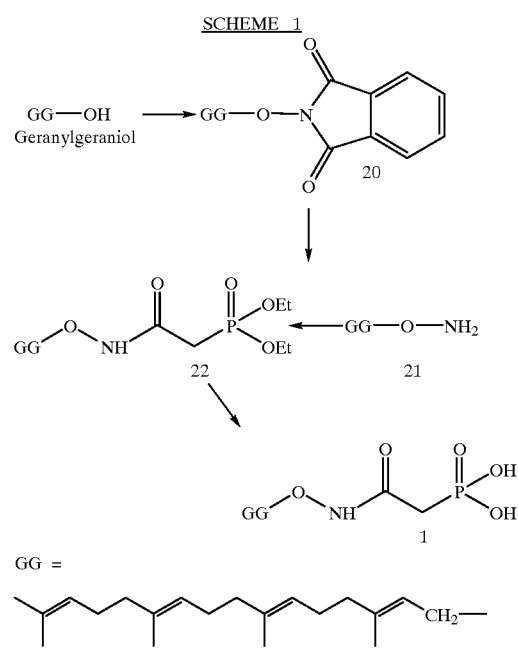

a) Synthesis of (E,E,E)-N-(3,7,11,15-tetramethyl-2,6,10,14-hexadecatetraenyloxy)phthalimide (20).

A solution of N-hydroxyphthalimide (1.12 g, 6.88 mmol), triphenylphosphine (1.81 g, 6.88 mmol) and diethylazodicarboxylate (1.19 mL, 7.57 mmol) in anhydrous THF (60 mL) was treated with geranylgeraniol (2.0 g, 6.88 mmol) and the resulting mixture was stirred for 18 h at rt. After addition of triphenylphosphine (0.905 g, 3.44 mmol) and diethylazodicarboxylate (0.595 mL, 3.78 mmol), the mixture was stirred at rt for another 24 h. The solvent was evaporated and the residue was purified on 230–400 mesh silica gel (Macherey-Nagel Silica Gel 60 Art. Nr. 81538) eluting with CH$_2$Cl$_2$-hexane (6:4) and collecting 10 mL fractions. The appropriate fractions were combined and evaporated to give the intermediate 20 (2.63 g, 88%) as a white solid: mp 40–41° C.; $^1$H-NMR (CDCl$_3$, 80 Mhz) δ 1.58 (s, 9H, 3×CH$_3$), 1.67 (s, 3H, CH$_3$), 1.71 (s, 3H, CH$_3$), 2.03 (m, 12H, 6×CH$_2$), 4.71 (d, 2H, J=7.2 Hz, CH$_2$), 5.07 (br, 3H, 3×CH), 5.52 (t, 1H, J=7.2 Hz, CH), 7.73 (m, 4H, Ar); Anal. Calcd for C$_{28}$H$_{37}$NO$_3$ (MW 435.3); C, 77.26; H, 8.50; N, 3.22. Found: C, 77.38; H, 8.38; N, 3.04.

b) Synthesis of (E,E,E,)-3,7,11,15-tetramethyl-2,6,10,14-hexadecatetraenyloxyamine (21).

Hydrazine monohydrate (0.44 mL, 906 mmol) was added to a solution of 20 (2.63 g, 6.04 mmol) in EtOH (130 mL) and the resulting mixture was stirred at rt for 18 h. After filtration of a white solid formed, the solution was evaporated and the resulting oily crude residue was purified by column chromatography on reverse phase silica gel (Macherey-Nagel Polygosil® 60-4063 C$_{18}$ Art. Nr. 71150) eluting with CH$_3$CN-H$_2$O (7:1) and colleting 10 mL fractions. The appropriate fractions were combined, evaporated, and pump-dried to give the intermediate 21 (1.07 g, 57%) as an oil: $^1$H-NMR (CDCl$_3$, 80 Mhz) δ1.60 (s, 9 H, 3×CH$_3$), 1.69 (s, 6 H, 2×CH$_3$), 2.04 (m, 12 H, 6×CH$_2$), 4.17 (d, 2 H, J=7.2 Hz, CH$_2$), 5.08 (br, 3 H, 3×CH), 5.29 (t, 1 H, J=7.2 Hz, CH); MS m/e 306 (M+H)$^+$.

c) Synthesis of diethyl (E,E,E)-{2-oxo-2-[[(3,7,11,15-tetramethyl-2,6,10,14-hexadecatetraenyl)oxy]amino]ethyl}phosphonate (22).

A solution of compound 21 (0.200 g, 0.65 mmol), diethylphosphonoacetic acid (0.139 g, 0.71 mmol), prepared as disclosed by M. P. Cooke, K. B. Bicunas, *Synthesis*, 283, 1981 and 1-hydroxybenzotriazole (0.31 g, 0.98 mmol) in anhydrous THF (10 ml) was treated with 1-(3-dimethylaminopropyl)-3-ethylcarbodiimide hydrochloride (0.150 g, 0.78 mmol). The mixture was stirred at rt for 8 h, and the solvent was evaporated under reduced pressure. The residue was purified by column chromatography on 230–400 mesh silica gel (Macherey-Nagel Silica Gel 60 Art. Nr. 81538) eluting with AcOEt-hexane (1:1) and collecting 3 mL fractions. The appropriate fractions were combined, evaporated, and pump-dried to give intermediate 22 (0.208 g, 66%) as an oil: $^1$H-NMR (CDCl$_3$, 80 Mhz) δ1.33 (t, 6 H, J=7.2 Hz, 2×CH$_3$CH$_2$), 1.60 (s, 9 H, 3×CH$_3$), 1.67 (s, 3 H, CH$_3$), 1.71 (s, 3 H, CH$_3$), 2.04 (m, 12 H, 6×CH$_2$), 2.81 (d, 2 H, J=20 Hz, CH$_2$P), 4.13 (q, 4 H, J=7.2 Hz, 2×CH$_3$CH$_2$), 4.41 (d, 2 H, J=7.2 Hz, CH$_2$), 5.07 (br, 3 H, 3×CH), 5.38 (t, 1 H, J=7.2 Hz, CH); MS (FAB$^+$) m/e 484 (M+H)$^+$.

Synthesis of 1. Bromotrimethylsilane (0.400 mL, 3 mmol) was aded to a stirred solution of compound 22 (0.290 g, 0.6 mmol) and 2,4,6-collidine (0.158 mL, 1.2 mmol) in anhydrous CH$_2$Cl$_2$ (6 mL); the resulting mixture was stirred at rt for 18 h. After evaporation of the solution, the residue was treated with an aqueous solution of KOH 0.9 N (5.0 mL) and then stirred at rt for 3 h. The solution was evaporated and the resulting crude residue was purified by column chromatography on reverse phase silica gel (Macherey-Nagel Polygosil® 60-4063 C$_{18}$ Art. Nr. 71150) eluting with MeOH-H$_2$O (2.5:3) and collecting 2 mL fractions. The appropriate fractions were combined, evaporated, lyophilized, and pump-dried to give 1 (0.125 g, 41%) as a very hygroscopic white lyophilate: $^1$H-NMR (D$_2$O, 80 Mhz) δ1.56 (s, 9 H, 3×CH$_3$), 1.62 (s, 3 H, CH$_3$), 1.72 (s, 3 H, CH$_3$), 202 (m, 12 H, 6×CH$_2$), 2.48 (d, 2 H, J=20 Hz, CH$_2$P), 4.40 (d, 2 H, J=7.2 Hz, CH$_2$), 5.07 (br, 3 H, 3×CH), 5.40 (t, 1 H, J=7.2 Hz, CH); MS (FAB$^+$) m/e 504 (M+H)$^+$.

EXAMPLE 2

Synthesis of the monosodium salt of ethyl (E,E,E)-{2-oxo-2-[[(3,7,11,15-tetramethyl-2,6,10,14-hexadecatetraenyl)oxy]amino]ethyl}phosphonate

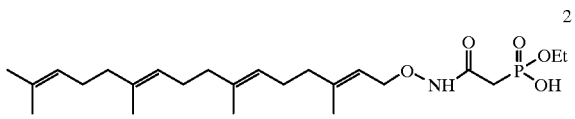
2

An aqueous solution of NaOH 1 H (1.6 mL) was added to a stirred solution of intermediate 22 (0.193 g, 0.4 mmol) in dioxane (4 mL); the resulting mixture was stirred at 40° C. for 4 h, treatd with another 2 mL of NaOH 1 N and then stirred at 40° C. for 12 h. The solvent was removed under reduced pressure and the crude residue was purified by column chromatography on reverse phase solica gel (Macherey-Nagel Polygosil® 60-4063 $C_{18}$ Art. Nr. 71150) eluting with MeOH-$H_2O$ (3:2) and collecting 2 mL fractions. The appropriate fractions were combined, evaporated, lyophilized, and pump-dried to give 3 (0.137 g, 72) as a very hygroscopic white lyophilate: $^1$H-NMR (CD$_3$OD, 80 Mhz) δ1.24 (t, 3 H, J=7.2 Hz, C$\underline{H}_3$CH$_2$), 1.59 (s, 9 H, 3×CH$_3$), 1.66 (s, 3 H, CH$_3$), 1.69 (s, 3 H, CH$_3$), 2.03 (m, 12 H, 6×CH$_2$), 2.19 (d, 2 H, J=20 Hz, CH$_2$P), 3.93 (q, 2 H, J=7.2 Hz, CH$_3$C$\underline{H}_2$), 4.34 (d, 2 H, J=7.2 Hz, CH$_2$), 5.08 (br, 3 H, 3×CH), 5.42 (t, 1 H, J=7.2 Hz, CH); MS (FAB$^+$) m/e 478 (M+H)$^+$, 500 (M+na)$^+$.

EXAMPLE 3

Synthesis of the dipotassium salt of (E,E,E)-1-[[(3,7,11,15-tetramethyl-2,6,10,14-hexadecatetracnyl)oxy]aminocarbonyl]ethylphosphonic acid.

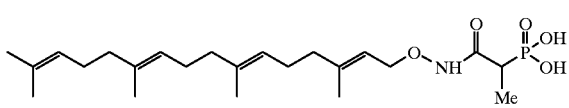
3

Compound 3 was prepared as shown in SCHEME 2

SCHEME 2

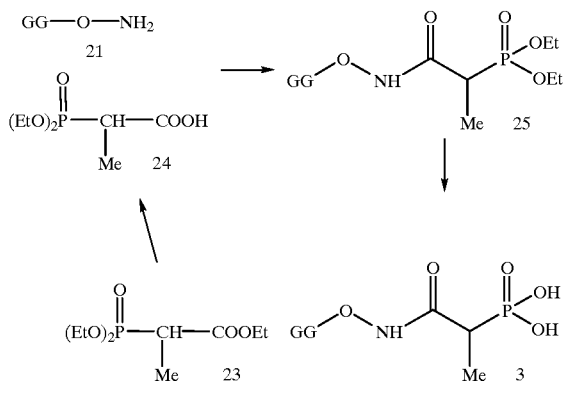

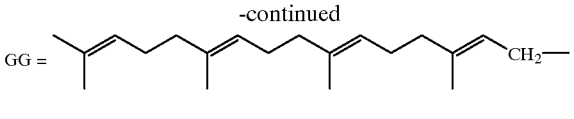

a) Synthesis of intermediate 24 (2-(diethylphosphone)propionic acid).

A solution containing KOH (2.35 g, 42 mmol) absolute EtOH (7 mL) and H$_2$O (3 mL) was added dropwise to triethyl 2-phosphonopropionate (9 mL, 42 mmol) and the resulting mixture was stirred at rt for 24 h. The solvents were removed under reduced presure and the oily crude residue was cooled at 0° C. and triturated with Et$_2$O (3×130 mL) which was discarded. The resulting residue was dissolved in H$_2$O (30 mL) and acidified to pH 1 with HCl 6 M. The solution was then saturated with solid Nacl and extracted with CH$_2$Cl$_2$ (2×25 mL). The organic phase was dried and evaporated to give intermediate 24 (7.1 g, 80%) as an oil: $^1$H-NMR (CDCl$_3$, 80 Mhz) δ1.34 (t, 6 H, J=7.2 Hz, 2×C$\underline{H}_3$CH$_2$), 1.42 (dd, 3 H, J=7.2, 17.5 Hz, CH$_3$), 3.04 (dq, 1 H, J=7.2, 24 Hz, CH), 4.11 (q, 2 H, J=7.2 Hz, CH$_3$C$\underline{H}_2$), 4.13 (q, 2 H, J=7.2 Hz, CH$_3$C$\underline{H}_2$); MS m/e 2 H (M+H)$^+$.

b) Synthesis of diethyl (E,E,E)-1-[[(3,7,11,15-tetramethyl-2,6,10,14-hexadecatetraenyl)oxy]aminocarbonyl]ethylphosphonate (25)

A solution of intermediate 21 (0.400 g, 1.31 mmol), intermediate 24 (0.302 g, 1.44 mmol) and 1-hydroxybenzotriazole (0.265 g, 1.96 mmol) in anhydrous THF (15 ml) was treated with 1-(3-dimethylaminopropyl)-3-ethylcarbodiimide hydrochloride (0.301 g, 1.57 mmol). the mixture was stirred at rt for 18 h, and the solvent was evaporated under reduced pressure. The residue was purified by column chromatography on 230–400 mesh silica gel (Macherey-Nagel Silica Gel 60 art. Nr. 81538) eluting with AcOEt-hexane (1:1) and collecting 3 mL fractions. The appropriate fractions were combined, evaporated, and pump-dried to give intermediate 25 (0.544 g, 83%) as an oil: $^1$H-NMR (CDCl$_3$, 80 Mhz) δ1.38 (m, 9 H, 2×C$\underline{H}_3$CH$_2$+CH$_3$), 1.59 (s, 9 H, 3×CH$_3$), 1.67 (s, 3 H, CH$_3$), 1.70 (s, 3 H, CH$_3$), 2.02 (m, 12 H, 6×CH$_2$), 2.56 (m, 1 H, CH), 4.04 (q, 2 H, J=7.2 Hz, CH$_3$C$\underline{H}_2$), 4.06 (q, 2 H, J=7.2 Hz, CH$_3$C$\underline{H}_2$), 4.41 (d, 2 H, J=7.2 Hz, CH$_2$), 5.09 (br, 3 H, 3×CH), 5.41 (t, 1 H, J=7.2 Hz, CH); MS (FAB$^+$) m/c 498 (M+H)$^+$.

Synthesis of 3. Bromotrimethysilane (0.527 mL, 4 mmol) was added to a stirred solution of compound 25 (0.400 g, 0.8 mmol) and 2,4,6-collidine (0.211 mL, 1.6 mmol) in anhydrous CH$_2$Cl$_2$ (10 mL); the resulting mixture was stirred at rt for 18 h. After evaporation of the solution, the residue was treated with an aqueous solution of KOH 1 N (6.1 mL) and then stirred at rt for 3 h. The solution was evaporated and the resulting crude residue was purified by column chromatography on reverse phase solica gel (Macherey-Nagel Polygosil® 60-4063 $C_{18}$ Art. Nr. 71150) eluting with MeOH-H$_2$O (1.5:1) and collecting 2 mL fractions. The appropriate fractions were combined, evaporated, lyophilized, and pump-dried to give 3 (0.221 g, 53%) as a very hygroscopic white lyophilate: $^1$H-NMR (CD$_3$OD, 80 Mhz) δ1.35 (dd, 3 H, J=7.2, 15.2 Hz, CH$_3$), 1.60 (s, 9 H, 3×CH$_3$), 1.67 (s, 3 H, CH$_3$), 1.72 (s, 3 H, CH$_3$). 2.04 (m, 12 H, 6×CH$_2$), 2.51 (dq, 1 H, J=7.2, 20 Hz, CH), 4.40 (d, 2 H, J=7.2 Hz, CH$_2$), 5.10 (br, 3 H, 3×CH), 5.41 (t, 1 H, J=7.2 Hz, CH); MS (FAB$^+$) m/e 518 (M+H)$^+$.

EXAMPLE 4

Synthesis of the dipotassium salt of (E,E,E)-1-[[(3,7,11,15-tetramethyl-2,6,10,14-hexadecatetraenyl)oxy]aminocarbonyl]phopylphosphonic acid.

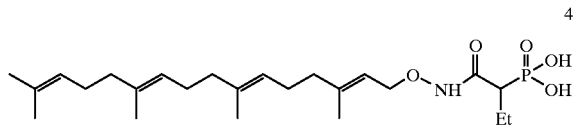

Compound 4 was prepared as shown in SCHEME 3

SCHEME 3

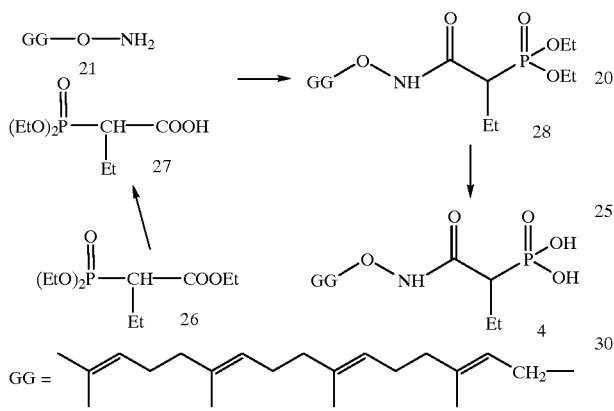

a) Synthesis of intermediate 27 (2-(diethylphosphono)butyric acid).

A solution containing KOH (2.35 g, 42 mmol) absolute EtOH (7 mL) and $H_2O$ (3 mL) was added dropwise to triethyl 2-phosphonobutyrate (9.9 mL, 42 mmol) and the resulting mixture was stirred at rt for 24 h. The solvents were removed under reduced pressure and the solid crude residue was triturated with $Et_2O$ (3×130 mL) which was discarded. The resulting residue was dissolved in $H_2O$ (30 mL) and acidified to pH 1 with HCl 6 M. The solution was then saturated with solid NaCl and extracted with $CH_2Cl_2$ (3×25 mL). The organic phase was dried and evaporated to give intermediate 27 (8.5 g, 90%) as an oil: $^1$H-NMR (CDCl$_3$, 80 Mhz) δ1.01 (t, 3 H, J=7.2 Hz, C$\underline{H}_3$CH$_2$), 1.32 (t, 6 H, J=7.2 Hz, 2×C$\underline{H}_3$CH$_2$), 1.89 (m, 2 H, CH$_3$CH$_2$), 2.87 (dt, 1 H, J=7.2, 22 Hz, CH), 4.14 (m, 4 H, 2×CH$_3$C$\underline{H}_2$); MS m/e 225 (M+H)$^+$.

Synthesis of diethyl (E,E,E)-1-[[(3,7,11,15-tetramethyl-2,6,10,14-hexadecatetraenyl)oxy]aminocarbonyl]propylphosphonate (28)

A solution of intermediate 21 (0.400 g, 1.31 mmol), intermediate 27 (0.322 g, 1.44 mmol) and 1-hydroxybenzotriazole (0.265 g, 1.96 mmol) in anhydrous THF (15 ml) was treated with 1-(3-dimethylaminopropyl)-3-ethylcarbodiimide hydrochloride (0.301 g, 1.57 mmol). The mixture was stirred at rt for 18 h, and the solvent was evaporated under reduced pressure. The residue was purified by column chromatography on 230–400 mesh silica gel (Macherey-Nagel Silica Gel 60 Art. Nr. 81538) eluting with AcOEt-hexane (1:1) and collecting 3 mL fractions. The appropriate fractions were combined, evaporated, and pump-dried to give intermediate 28 (0.511 g, 76%) as an oil:

$^1$H-NMR (CDCl$_3$, 80 Mhz) δ0.99 (t, 3 H, J=7.2 Hz, C$\underline{H}_3$CH$_2$), 1.28 (t, 3 H, J=7.2 Hz, C$\underline{H}_3$CH$_2$), 1.30 (t, 3 H, J=7.2 Hz, C$\underline{H}_3$CH$_2$), 1.59 (s, 9 H, 3×CH$_3$), 1.68 (s, 3 H, CH$_3$), 1.70 (s, 3 H, CH$_3$), 2.01 (m, 14 H, 6×CH$_2$+CH$_3$C$\underline{H}_2$), 2.55 (dt, 1 H, J=7.2, 22 Hz, CH), 4.15 (m, 4 H, 2×CH$_3$C$\underline{H}_2$) 4.41 (d, 2 H, J=7.2 Hz, CH$_2$), 5.10 (br, 3 H, 3×CH), 5.41 (t, 1 H, J=7.2 Hz, CH); MS (FAB$^+$) m/e 512 (M+H)$^+$.

Synthesis of 4. Bromotrimethylsilane (0.528 mL, 4 mmol) was added to a stirred solution of compound 28 (0.410 g, 0.8 mmol) and 2,4,6-collidine (0.211 mL, 1.6 mmol) in anhydrous $CH_2Cl_2$ (10 mL); the resulting mixture was stirred at rt for 18 h. After evaporation of the solution, the residue was treated with an aqueous solution of KOH 1 N (6.1 mL) and then stirred at rt for 3 H. The solution was evaporated and the resulting crude residue was purified by column chromatography on reverse phase silica gel (Macherey-Nagel Polygosil® 60-4063 C$_{18}$ Art. Nr. 71150) eluting with MeOH-H$_2$O (1.5:1) and collecting 2 mL fractions. The appropriate fractions were combined, evaporated, lyophilized, and pump-dried to give 4 (0.235 g, 55%) as a very hygroscopic white lyophiliate: $^1$H-NMR (CD$_3$OD, 80 Mhz) δ0.99 (t, 3 H, J=7.2 Hz, C$\underline{H}_3$CH$_2$), 1.59 (s, 9 H, 3×CH$_3$), 1.66 (s, 3 H, CH$_3$), 1.72 (s, 3 H, CH$_3$), 2.03 (m, 14 H, 6×CH$_2$+CH$_3$C$\underline{H}_2$), 2.48 (m, 1 H, CH), 4.40 (d, 2 H, J=7.2 Hz, CH$_2$), 5.09 (br, 3 H, 3×CH), 5.40 (t, 1 H, J=7.2 Hz, CH); MS (FAB$^+$) m/e 532 (M+H)$^+$.

EXAMPLE 5

Synthesis of the dipotassium salt of (E,E,E)-{3-oxo-3-[[(3,7,11,15-tetramethyl-2,6,10,14-hexadecatetraenyl)oxy]amino]propyl}phosphonic acid

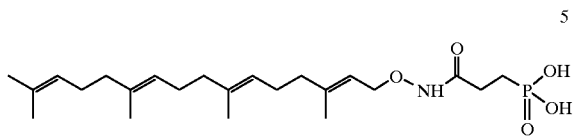

Compound 5 was prepared as shown in SCHEME 4

SCHEME 4

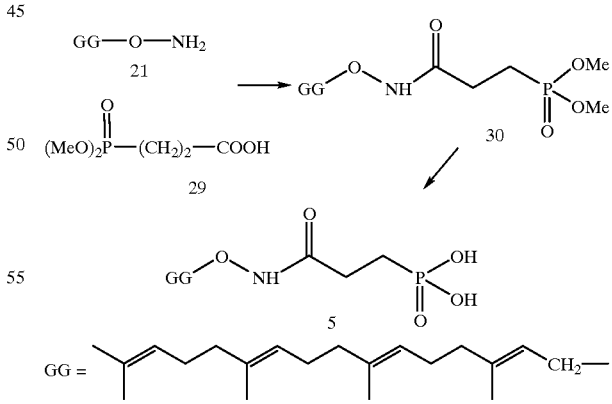

a) Synthesis of dimethyl (E,E,E)-{3-oxo-3-[[(3,7,11,15-tetramethyl-2,6,10,14-hexadecatetracnyl)oxy]amino]propyl}phosphonate (30)

A solution of intermediate 21 (0.400 g, 1.31 mmol), intermediate 29 (3-(dimethylphosphono)propionic acid), (0.262 g, 1.44 mmol), prepared as disclosed by D. V. Patel, R. J. Schmidt, S. A. Biller, E. M. Gordon, S. S. Robinson, V. Manne, J. Med. Chem., 38, 2906–2921, 1995, and 1-hydroxybenzotriazole (0.265 g, 1.96 mmol) in anhydrous THF (20 ml) was treated with 1-(3-dimethylaminopropyl)-3-ethylcarbodiimide hydrochloride (0.301 g, 1.57 mmol). The mixture was stirred at rt for 24 h, and the solvent was evaporated under reduced pressure. The residue was purified by column chromatography on 230–400 mesh silica gel (Macherey-Nagel Silica Gel 60 art. Nr. 81538) eluting with CHCl3-MeOH (98:2) and collecting 3 mL fractions. The appropriate fractions were combined, evaporated, and pump-dried to give intermediate 30 (0.250 g, 40%) as an oil: 1H-NMR (CDCl3, 80 Mhz) δ1.59 (s, 9 H, 3×CH3), 1.67 (s, 3 H, CH3), 1.70 (s, 3 H, CH3), 2.10 (m, 14 H, 7×CH2), 2.43 (m, 2 H, CH2), 3.72 (d, 6 H, J=10.4 Hz, 2×CH3), 4.37 (d, 2 H, J=7.2 Hz, CH2), 5.08 (br, 3 H, 3×CH), 5.35 (t, 1 H, J=7.2 Hz, CH); MS (FAB+) m/e 470 (M+H)+.

Synthesis of 5. Bromotrimethylsilane (0.320 mL, 2.45 mmol) was added to a stirred solution of compound 30 (0.230 g, 0.49 mmol) and 2,4,6-collidine (0.13 mL, 0.98 mmol) in anhydrous $CH_2Cl_2$ (6 mL); the resulting mixture was stirred at rt for 18 h. After evaporation of the solution, the residue was treated with an aqueous solution of KOH 1.0 N (3.7 mL) and then stirred at rt for 3 h. The solution was evaporated and the resulting crude residue was purified by column chromatography on reverse phase silica gel (Macherey-Nagel Polygosil® 60-4063 $C_{18}$ Art. Nr. 71150) eluting with MeOH-$H_2O$ (2.5:3) and collecting 2 mL fractions. The appropriate fractions were combined, evaporated, lyophilized, and pump-dried to give 5 (0.158 g, 62%) as a very hygroscopic white lyophilate: $^1$H-NMR ($CD_3OD$, 80 Mhz) δ1.59 (s, 9 H, 3×$CH_3$), 1.66 (s, 3 H, $CH_3$), 1.70 (s, 3 H, $CH_3$), 1.75 (m, 2 H, $CH_2$), 2.10 (m, 12 H, 6×$CH_2$), 2.42 (m, 2 H, $CH_2$), 4.34 (d, 2 H, J=7.2 Hz, $CH_2$), 5.07 (br, 3 H, 3×CH), 5.39 (t, 1 H, J=7.2 Hz, CH); MS (FAB$^+$) m/e 518 (M+H)$^+$.

EXAMPLE 6

Synthesis of the trisodium salt of (E,E,E)-3-oxo-2-(phosphonomethyl)-3-[[(3,7,11,15-tetramethyl-2,6,10,14-hexadecatetraenyl)oxy]amino]propanoic acid.

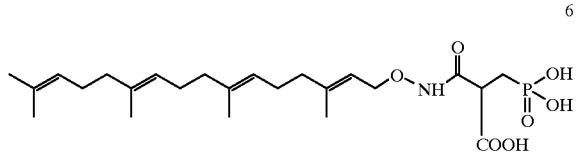

Compound 6 was prepared as shown in SCHEME 5

SCHEME 5

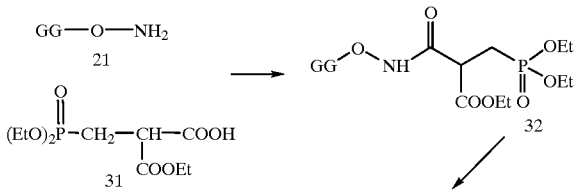

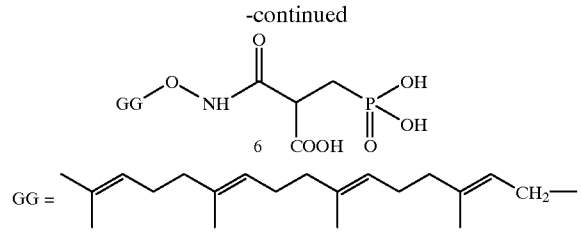

a) Synthesis of ethyl (E,E,E)-3-oxo-2-(diethylphosphonomethyl)-3-[[(3,7,11,15-tetramethyl-2,6,10,14-hexadecatetraenyl)oxy]amino]propanoate (32)

a solution of intermediate 21 (0.400 g, 1.31 mmol), intermediate 31 [(diethoxyphosphinyl)methyl]propanedioic acid monoethyl ester (0.406 g, 1.44 mmol), prepared as disclosed by D. V. Patel, R. J. Schmidt, S. A. Biller, E. M. Gordon, S. S. Robinson, V. Manne, J. Med. Chem., 38, 2906–2921, 1995, and 1-hydroxybenzotriazole (0.265 g, 1.96 mmol) in anhydrous THF (20 ml) was treated with 1-(3-dimethylaminopropyl)-3-ethylcarbodiimide hydrochloride (0.301 g, 1.57 mmol). The mixture was stirred at rt for 24 h, and the solvent was evaporated under reduced pressure. The residue was purified by column chromatography on 230–400 mesh silica gel (Macherey-Nagel Silica Gel 60 Art. Nr. 81538) eluting with AcOEt-hexane (1:1) and collecting 3 mL fractions. the appropriate fractions were combined, evaporated, and pump-dried to give intermediate 32 (0.705 g, 94%) as an oil: $^1$H-NMR (CDCl$_3$, 80 Mhz) δ1.27 (t, 3 H, J=7.2 Hz, C$\underline{H}_3$CH$_2$), 1.28 (t, 3 H, J=7.2 Hz, C$\underline{H}_3$CH$_2$), 1.30 (t, 3 H, J=7.2 Hz, C$\underline{H}_3$CH$_2$), 1.59 (s, 9 H, 3×CH$_3$), 1.67 (s, 3 H, CH$_3$), 1.71 (s, 3 H, CH$_3$), 2.05 (m, 12 H, 6×CH$_2$), 2.54 (m, 2 H, CH$_2$), 3.70 (m, 1 H, CH), 4.16 (m, 6 H, 3×CH$_3$C$\underline{H}_2$), 4.42 (d, 2 H, J=7.2 Hz, CH$_2$), 5.08 (br, 3 H, 3×CH), 5.39 (t, 1 H, J=7.2 Hz, CH); MS (FAB$^+$) m/e 570 (M+H)$^+$.

Synthesis of 6. Bromotrimethylsilane (0.460 mL, 3.5 mmol) was added to a stirred solution of compound 30 (0.400 g, 0.70 mmol) and 2,4,6-collidine (0.185 mL, 1.4 mmol) in anhydrous $CH_2Cl_2$ (15 mL); the resulting mixture was stirred at rt for 18 h. After evaporation of the solution, the residue was treated with an aqueous solution of NaOH 1.0 N (6 mL) and then stirred at rt for 20 h. The solution was evaporated and the resulting crude residue was purified by column chromatography on reverse phase silica gel (Macherey-Nagel Polygosil® 60-4063 $C_{18}$ art. Nr. 71150) eluting with MeOH-$H_2O$ (1:1) and collecting 2 mL fractions. The appropriate fractions were combined, evaporated, lyophilized, and pump-dried to give 6 (0.173 g, 45%) as a very hygroscopic white lyophilate: $^1$H-NMR ($D_2O$, 80 Mhz) δ1.55 (s, 9 H, 3×CH$_3$), 1.62 (s, 3 H, CH$_3$), 1.71 (s, 3 H, CH$_3$), 2.02 (m, 12 H, 6×CH$_2$), 2.63 (m, 2 H, CH$_2$), 3.48 (m, 1 H, CH), 4.43 (d, 2 H, J=7.2 Hz, CH$_2$), 5.07 (br, 3 H, 3×CH), 5.40 (t, 1 H, J=7.2 Hz, CH); MS (FAB$^+$) m/e 552 (M+H)$^+$.

EXAMPLE 7

Synthesis of the dipotassium salt of (E,E,E)-[2-oxo-2-[(3,7,11,15-tetramethyl-2,6,10,14-hexadecatetraenyl)amino]ethyl]phosphonic acid.

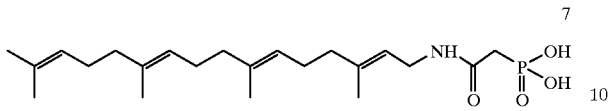

compound 7 was prepared as shown in SCHEME 6

SCHEME 6

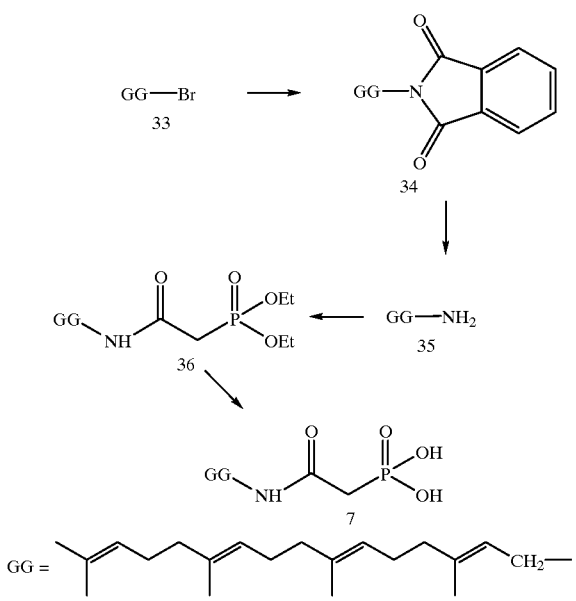

a) Synthesis of (E,E,E)-N-(3,7,11,15-tetramethyl-2,6,10,14-hexadecatetraenyl)-phthalimide (34)

A solution of intermediate 33 (1 g, 2.83 mmol, prepared as disclosed by T. Fukuda, S. Kobayashi, H. Yukimasa, S. Terao, M. Fujino, T. Shiba, I. Saiki, I. Azuma, Y. Yamamura, *Bull. Chem. Soc. Jpn.,* 54, 3530–3535, 1981, in anhydrous DMF (15 mL) at room temperature under argon was treated with potassium phthalimide (0.575 g, 3.10 mmol), and the resulting mixture was stirred for 18 h at rt. The solvent was evaporated and the residue was purified by column chromatography on 230–400 mesh silica gel (Macherey-Nagel Silica Gel 60 art. Nr. 81538) eluting with hexane-$CH_2Cl_2$ (5.2) and collecting 10 mL fractions. The appropriate fractions were combined and evaporated to give the intermediate 34 (1.1 g, 92%) as a white solid: mp 32 C; $^1$H-NMR ($CDCl_3$, 80 Mhz) δ 1.57 (s, 9H, 3×$CH_3$) 1.66 (s, 3H, $CH_3$), 1.82 (s, 3H, $CH_3$), 1.98 (m, 12H, 6×$CH_2$), 4.25 (d, 2H, J=7.2 Hz, $CH_2$), 5.07 (br, 3H, 3×CH), 5.26 (t, 1H, J=7.2 Hz, CH), 7.71 (m, 4H, Ar); MS ($FAB^+$) m/e 420 $(M+H)^+$.

b) Synthesis of (E,E,E)-3,7,11,15-tetramethyl-2,6,10,14-hexadecatetraenylamine (35)

Hydrazine monohydrate (0.138 ml, 2.86 mmol) was added to a solution of intermediate 34 (0.80 g, 1.9 mmol) in EtOH (90 mL), and the resulting mixture was stirred at room temperature for 24 h. After filtration of a white solid, the solution was evaporated and the residue was extracted with $Et_2O$ (2×20 mL). The organic layers were filtered and evaporated to give intermediate 35 (0.520 g, 95%) as an oil, which was used for the following reaction without any further purification; $^1$H-NMR ($CD_3OI$), 80 Mhz) δ 1.59 (s, 9H, 3×$CH_3$), 1.65 (s, 6H, 2×$CH_3$), 2.02 (m, 12H, 6×$CH_2$), 3.27 (d, 2H, J=7.2 Hz, $CH_2$), 5.12 (br, 3H, 3×CH), 5.25 (t, 1H, J=7.2 Hz, CH); MS ($FAB^+$) m/e 290 $(M+H)^+$.

c) Synthesis of diethyl (E,E,E)-[2-oxo-2-[(3,7,11,15-tetramethyl-2,6,10,14-hexadecatetraenyl)amino]ethyl]phosphonate (36)

A solution of compound 35 (0.360 g, 1.24 mmol), diethylphosphonoacetic acid (0.266 g, 1.36 mmol, prepared as disclosed by M. P. Cooke, K. B. Bicunas, *Synthesis,* 283, 1981, and 1-hydroxybenzotriazole (0.251 g, 1.86 mmol) in anhydrous THF (15 ml) was treated with 1-(3-dimethylaminopropyl)-3-ethylcarbodiimide hydrochloride (0.285 g, 1.49 mmol). The mixture was stirred at rt for 24 h, and the solvent was evaporated under reduced pressure. The residue was purified by column chromatography on 230–400 mesh silica gel (Macherey-Nagel Silica Gel 60 Art. Nr. 81538) eluting with $CH_2Cl_2$-hexane-MeOH (98:70:4) and collecting 4 mL fractions. The appropriate fractions were combined, evaporated, and pump-dried to give intermediate 36 (0.464 g, 80%) as an oil: $^1$H-NMR ($CDCl_3$, 80 Mhz) δ 1.33 (t, 6H, J=7.1 Hz, 2×C$\underline{H}_3CH_2$), 1.60 (s, 9H, 3×$CH_3$), 1.67 (s, 6H, 2×$CH_3$), 2.02 (m, 12H, 6×$CH_2$), 2.83 (d, 2H, J=20 Hz, $CH_2P$), 3.86 (d, 2H, J=7.1 Hz, $CH_2$), 4.14 (q, 4H, J=7.1 Hz, 2×$CH_3C\underline{H}_2$), 5.10 (br, 3H, 3×CH), 5.20 (t, 1H, J=7.1 Hz, CH); MS ($FAB^+$) m/e 468 $(M+H)^+$.

Synthesis of 7. Bromotrimethylsilane (0.282 mL, 2.14 mmol) was added to a stirred solution of compound 36 (0.200 g, 0.428 mmol) and 2,4,6-collidine (0.113 mL, 0.856 mmol) in anhydrous $CH_2Cl_2$ (6 mL); the resulting mixture was stirred at rt for 18 h. After evaporation of the solution, the residue was treated with an aqueous solution of KOH 1.0 N (3.2 mL) and then stirred at rt for 3 h. The solution was evaporated and the resulting crude residue was purified by column chromatography on reverse phase silica gel (Macherey-Nagel Polygosil® 60-4063 $C_{18}$ Art. Nr. 71150) eluting with MeOH-$H_2O$ (1:1) and collecting 2 mL fractions. The appropriate fractions were combined, evaporated, lyophilized, and pump-dried to give 7 (0.194 g, 93%) as a very hygroscopic white lyophilate: $^1$H-NMR ($CD_3OD$, 80 Mhz) δ 1.54 (s, 9H, 3×$CH_3$) 1.61 (s, 6H, 2×$CH_3$), 1.95 (m, 12H, 6×$CH_2$), 2.49 (d, 2H, J=19 Hz, $CH_2P$), 3.75 (d, 2H, J=7.1 Hz, $CH_2$), 5.03 (br, 3H, 3×CH), 5.20 (t, 1H, J=7.1 Hz, CH); MS ($FAB^+$) m/e 488 $(M+H)^+$.

EXAMPLE 8

Synthesis of the dipotassium salt of (E,E,E)-1-[(3,7,11,15-tetramethyl-2,6,10,14-hexadecatetraenyl)aminocarbonyl]ethylphosphonic acid.

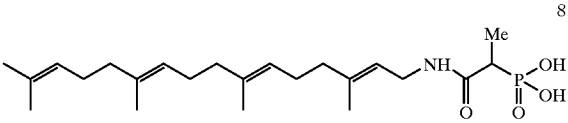

21

Compound 8 was prepared as shown in SCHEME 7

SCHEME 7

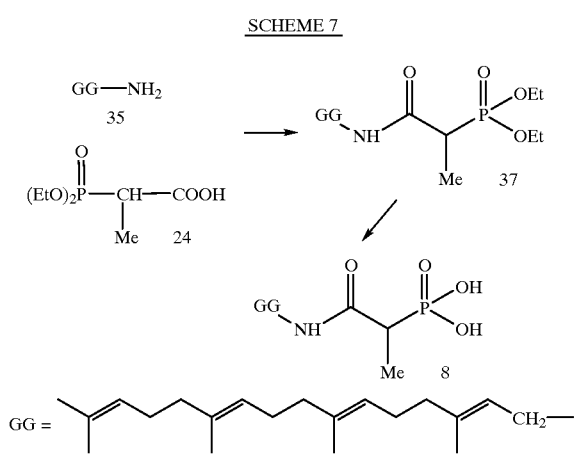

a) Synthesis of diethyl (E,E,E)-1-[(3,7,11,15-tetramethyl-2,6,10,14-hexadecatetraenyl) aminocarbonyl]ethylphosphonate (37)

A solution of intermediate 35 (0.400 g, 1.38 mmol), intermediate 24 (0.319 g, 1.52 mmol) and 1-hydroxybenzotriazole (0.280 g, 2.07 mmol) in anhydrous THF (18 ml) was treated with 1-(3-dimethylaminopropyl)-3-ethylcarbodiimide hydrochloride (0.318 g, 1.66 mmol). The mixture was stirred at rt for 18 h, and the solvent was evaporated under reduced pressure. The residue was purified by column chromatography on 230–400 mesh silica gel (Macherey-Nagel Silica Gel 60 Art. Nr. 81538) eluting with AcOEt-hexane (1:1) and collecting 3 mL fractions. The appropriate fractions were combined, evaporated, and pump-dried to give intermediate 37 (0.563 g, 83%) as an oil: $^1$H-NMR (CDCl$_3$, 80 Mhz) δ 1.37 (m, 9H, 2×C$\underline{H}_3$CH$_2$+CH$_3$), 1.59 (s, 9H, 3×CH$_3$), 1.68 (s, 6H, 2×CH$_3$), 2.01 (m, 12H, 6×Ch$_2$), 2.78 (m, 1H, CH), 3.85 (d, 2H, J=7.2 Hz, CH$_2$), 4.03 (q, 2H, J=7.2 Hz, CH$_3$C$\underline{H}_2$), 4.05 (q, 2H, J=7.2 Hz, CH$_3$C$\underline{H}_2$), 5.12 (br, 3H, 3×CH), 5.23 (t, 1H, J=7.2 Hz, CH); MS (FAB$^+$) m/e 482 (M+H)$^+$.

Synthesis of 8. Bromotrimethylsilane (0.410 ml, 3.1 mmol) was added to a stirred solution of compound 37 (0.300 g, 0.621 mmol) and 2,4,6-collidine (0.164 mL, 1.24 mmol) in anhydrous CH$_2$Cl$_2$ (6 mL); the resulting mixture was stirred at rt for 18 h. After evaporation of the solution, the residue was treated with an aqueous solution of KOH 1 N (4.7 mL) and then stirred at rt for 3 h. The solution was evaporated and the resulting crude residue was purified by column chromatography on reverse phase silica gel (Macherey-Nagel Polygosil® 60-4063 C$_{18}$ Art. Nr. 71150) eluting with MeOH-H$_2$O (1.5:1) and collecting 2 mL fractions. The appropriate fractions were combined, evaporated, lyophilized, and pump-dried to give 8 (0.233 g, 75%) as a very hygroscopic white lyophilate: $^1$H-NMR (CD$_3$OD, 80 Mhz) δ 1.35 (dd, 3H, J=7.2, 15.2 Hz, CH$_3$), 1.59 (s, 9H, 3×CH$_3$), 1.66 (s, 6H, CH$_3$), 2.01 (m, 12H, 6×CH$_2$), 2.54 (dq, 1H, J=7.2, 20 Hz, CH), 3.79 (d, 2H, J=7.2 Hz, CH$_2$), 5.13 (br, 3H, 3×CH), 5.23 (t, 1H, J=7.2 Hz, CH); MS (FAB$^+$) m/e 502 (M+H)$^+$.

22

EXAMPLE 9

Synthesis of the dipotassium salt of (E,E,E)-1-[(3,7,11,15-tetramethyl-2,6,10,14-hexadecatetraenyl) aminocarbonyl]propylphosphonic acid.

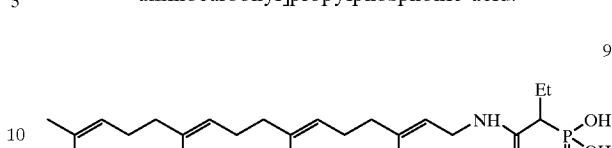

Compound 4 was prepared as shown in SCHEME 8

SCHEME 8

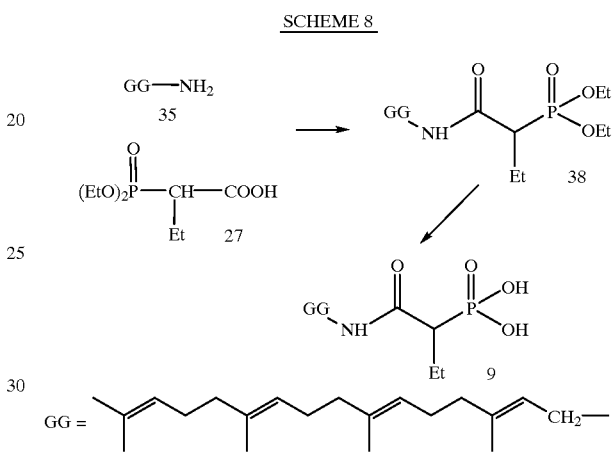

a) Synthesis of diethyl (E,E,E)-1-[(3,7,11,15-tetramethyl-2,6,10,14-hexadecatetraenyl) aminocarbonyl]propylphosphonate (38)

A solution of intermediate 35 (0.400 g, 1.38 mmol), intermediate 27 (0.340 g, 1.52 mmol) and 1-hydroxybenzotriazole (0.280 g, 2.07 mmol) in anhydrous THF (18 ml) was treated with 1-(3-dimethylaminopropyl)-3-ethylcarbodiimide hydrochloride (0.318 g, 1.66 mmol). The mixture was stirred at rt for 18 h, and the solvent was evaporated under reduced pressure. The residue was purified by column chromatography on 230–400 mesh silica gel (Macherey-Nagel Silica Gel 60 Art. Nr. 81538) eluting with AcOEt-hexane (1:1) and collecting 3 mL fractions. The appropriate fractions were combined, evaporated, and pump-dried to give intermediate 38 (0.518 g, 76%) as an oil; $^1$H-NMR (CDCl$_3$, 80 Mhz) δ 0.99 (t, 3H, J=7.2 Hz, C$\underline{H}_3$CH$_2$), 1.28 (t, 3H, J=7.2 Hz, C$\underline{H}_3$CH$_2$), 1.31 (t, 3H, J=7.2 Hz, C$\underline{H}_3$CH$_2$), 1.59 (s, 9H, 3×CH$_3$), 1.67 (s, 6H, 2×CH$_3$), 2.00 (m, 14H, 6×CH$_2$+CH$_3$C$\underline{H}_2$), 2.52 (dt, 1H, J=7,2 22 Hz, CH), 3.82 (d, 2H, J=7.2 Hz, CH$_2$), 4.10 (q, 2H, J=7.2, CH$_3$C$\underline{H}_2$), 4.12 (q, 2H, J=7.2, CH$_3$C$\underline{H}_2$), 5.08 (br, 3H, 3×CH), 5.19 (t, 1H, J=7.2 Hz, CH); MS (FAB$^+$) m/e 496 (M+H)$^+$.

Synthesis of 9. Bromotrimethylsilane (0.410 mL, 3.1 mmol) was added to a stirred solution of compound 38 (0.307 g, 0.621 mmol) and 2,4,6-collidine (0.164 mL, 1.24 mmol) in anhydrous CH$_2$CL$_2$ 96 mL); the resulting mixture was stirred at rt for 18 h. After evaporation of the solution, the residue was treated with an aqueous solution of KOH 1 N (4.7 mL) and then stirred at rt for 3 h. The solution was evaporated and the resulting crude residue was purified by column chromatography on reverse phase silica gel (Macherey-Nagel Polygosil® 60-4063 C$_{18}$ Art. Nr. 71150)

eluting with MeOH-H$_2$O (1.5:1) and collecting 2 mL fractions. The appropriate fractions were combined, evaporated, lyophilized, and pump-dried to give 9 (0.150 g, 47%) as a very hygroscopic white lyophilate: $^1$H-NMR (CD$_3$OD, 80 Mhz) δ 0.98 (t, 3H, J=7.2 Hz, CH$_3$CH$_2$), 1.59 (s, 9H, 3×CH$_3$), 1.67 (s, 6H, 2×CH$_3$), 2.02 (m, 14H, 6×CH$_2$+CH$_3$CH$_2$), 2.50 (m, 1H, CH), 3.81 (d, 2H, J=7.2 Hz, CH$_2$), 5.10 (br, 3H, 3×CH), 5.24 (t, 1H, J=7.2 Hz, CH); MS (FAB$^+$) m/e 516 (M+H)$^+$.

EXAMPLE 10

Synthesis of the dipotassium salt of (E,E,E)-[3-oxo-3-[(3,7,11,15-tetramethyl-2,6,10,14-hexadecatetraenyl)amino]propyl]phosphonic acid.

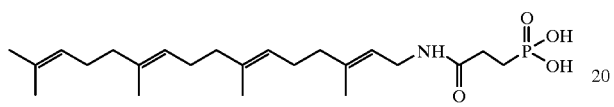

10

Compound 10 was prepared as shown in SCHEME 9

SCHEME 9

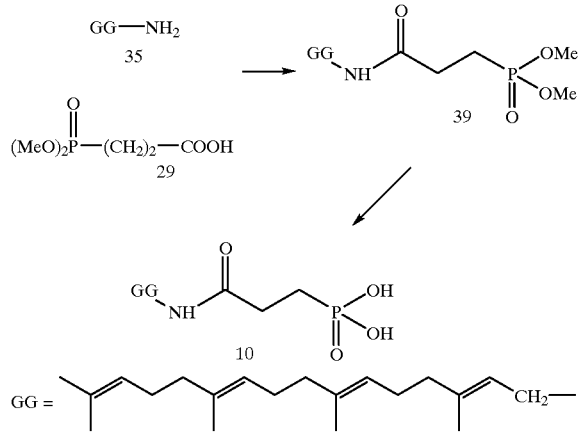

a) Synthesis of dimethyl (E,E,E)-[3-oxo-3-[(3,7,11,15-tetramethyl-2,6,10,14-hexadecatetraenyl)amino] propyl]phosphonate (39)

A solution of intermediate 35 (0.250 g, 0.86 mmol), intermediate 29 (0.172 g, 0.95 mmol) and 1-hydroxybenzotriazole (0.174 g, 1.29 mmol) in anhydrous THF (16 ml) was treated with 1-(3-dimethylaminopropyl)-3-ethylcarbodiimide hydrochloride (0.198 g, 1.03 mmol). The mixture was stirred at rt for 24 h, and the solvent was evaporated under reduced pressure. The residue was purified by column chromatography on 230–400 mesh silica gel (Macherey-Nagel Silica Gel 60 Art. Nr. 81538) eluting with CH$_2$Cl$_2$-hexane-MeOH (98:70:3) and collecting 3 mL fractions. The appropriate fractions were combined, evaporated, and pump-dried to give intermediate 39 (0.213 g, 55%) as an oil: $^1$H-NMR (CDCl$_3$, 80 Mhz) δ 1.60 (s, 9H, 3×CH$_3$), 1.67 (s, 6H, 2×CH$_3$), 2.08 (m, 14H, 7×CH$_2$), 2.42 (m, 2H, CH$_2$), 3.73 (d, 6H, J=10.8 Hz, 2×CH$_3$), 3.84 (d, 2H, J632 7.1 Hz, CH$_2$), 5.10 (br, 3H, 3×CH), 5.21 (t, 1H, J=7.1 Hz, CH); MS (FAB$^+$) m/e 454 (M+H)$^+$.

Synthesis of 10. Bromotrimethylsilane (0.280 ml, 2.10 mmol) was added to a stirred solution of compound 39 (0.190 g, 0.42 mmol) and 2,4,6-collidine (0.11 mL, 0.84 mmol) in anhydrous CH$_2$Cl$_2$(6 mL); the resulting mixture was stirred at rt for 18 h. After evaporation of the solution, the residue was treated with an aqueous solution of KOH 1.0 N (3.2 mL) and then stirred at rt for 3 h. The solution was evaporated and the resulting crude residue was purified by column chromatography on reverse phase silica gel (Macherey-Nagel Polygosil® 60-4063 C$_{18}$ Art. Nr. 71150) eluting with MeOH-H$_2$O (3:4) and collecting 2 mL fractions. The appropriate fractions were combined, evaporated, lyophilized, and pump-dried to give 10 (0.179 g, 85%) as a very hygroscopic white lyophilate: $^1$H-NMR (CD$_3$OD, 80 Mhz) δ 1.59 (s, 9H, 3×CH$_3$), 1.66 (s, 3H, CH$_3$), 1.68 (s, 3H, CH$_3$), 1.75 (m, 2H, CH$_2$), 2.05 (m, 12H, 6×CH$_2$), 2.42 (m, 2H, CH$_2$), 3.76 (d, 2H, J=7.1 Hz, CH$_2$), 5.11 (br, 3H, 3×CH), 5.22 (t, 1H, J=7.1 Hz, CH); MS (FAB$^+$) m/e 502 (M+H)$^+$.

EXAMPLE 11

Synthesis of the trisodium salt of (E,E,E)-3-oxo-2-(phosphonomethyl)-3-[(3,7,11,15-tetramethyl-2,6,10,14-hexadecatetraenyl)amino]propanoic acid.

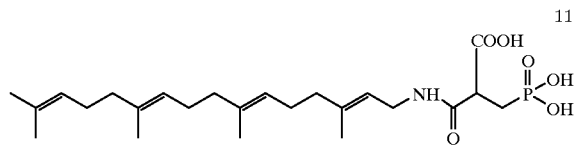

Compound 11 can be prepared according to the process of example 6 using intermediate 35 instead of intermediate 21 as a starting compound.

EXAMPLE 12

Synthesis of the tripotassium salt of (E,E,E)-[[(4,8,12,16-tetramethyl-3,7,11,15-heptadecatetraenyl)hydroxyphosphoryl]methyl]phosphonic acid.

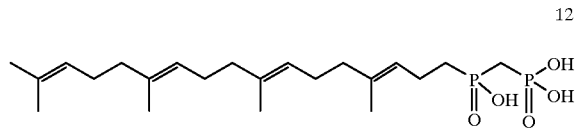

Compound 12 was prepared as shown in SCHEME 10

SCHEME 10

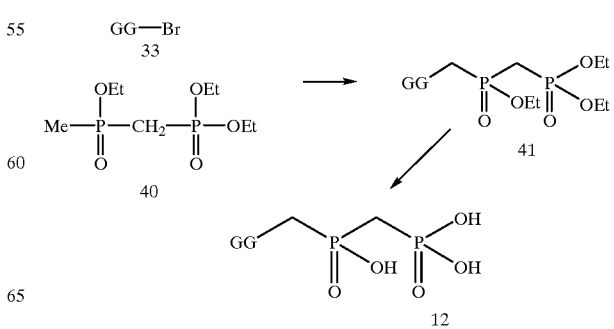

a) Synthesis of diethyl (E,E,E)-[[(4,8,12,16-tetramethyl-3,7,11,15-heptadecatetraenyl) ethoxyphosphoryl]methyl]phosphonate 941).

A solution of intermediate 40, diethyl ethoxy(methyl) phosphinoylmethylphosphonate, (0.242 g, 0.94 mmol, prepared as disclosed by M. Prashad, J. C. Tomesch, J. R. Wareing, T. Scallen, *Eur. J. Med. Chem*, 28, 527–531, 1993, in anhydrous THF (1 mL) was added dropwise to a stirred solution of sodium hydride (0.033 g, 1.1 mmol, 80% dispersion) in anhydrous THF (3 mL) under an argon atmosphere. The resulting solution was allowed to stir at room temperature for 2 h and then cooled to −78° C. Butyllithium (0.69 mL of 1.6 M hexane solution, 1.1 mmol) was then added dropwise and the solution, after stirring for 1 h at −78° C., was treated dropwise with intermediate 33 (0.400 g, 1.13 mmol) and then stirred for an additional 1 h at −78° C. The reaction mixture was quenched with acetic acid (0.136 g, 2.26 mmol), diluted with $CH_2Cl_2$ (15 mL) and washed with brine. The organic phase was dried and evaporated under reduced pressure. The residue was purified by column chromatography on 230–400 mesh silica gel (Macherey-Nagel Silica Gel 60 Art. Nr. 81538) eluting with hexane-AcOEt-MeOH (1:4:1) and collecting 3 mL fractions. The appropriate fractions were combined, evaporated, and pump-dried to give intermediate 41 (0.218 g, 36%) as an oil: $^1$H-NMR (CDCl$_3$, 80 Mhz) δ 1.34 (t, 9H, J=7.1 Hz, 3×C$\underline{H}_3$CH$_2$), 1.60 (s, 9H, 3×CH$_3$), 1.63 (s, 3H, CH$_3$), 1.68 (s, 3H, CH$_3$), 2.01 (m, 14H, 7×CH$_2$), 2.30 (m, 2H, CH$_2$), 2.40 (dd, 2H, J=16.4, 20.7 Hz, PCH$_2$P), 4.16 (m, 6H, 3×CH$_3$C$\underline{H}_2$), 5.10 (br, 4H, 4×CH); MS (FAB$^+$) m/e 531 (M+H)$^+$.

Synthesis of 12. Bromotrimethylsilane (0.23 mL, 1.7 mmol) was added to a stirred solution of compound 41 (0.180 g, 0.34 mmol) and 2,4,6-collidine (0.09 mL, 0.68 mmol) in anhydrous $CH_2Cl_2$ (6 mL); the resulting mixture was stirred at rt for 18 h. After evaporation of the solution, the residue was treated with an aqueous solution of KOH 1.0N (2,6 mL) and then stirred at rt for 3 h. The solution was evaporated and the resulting crude residue was purified by column chromatography on reverse phase silica gel (Macherey-Nagel Polygosil® 60-4063 C$_{18}$ Art. Nr. 71150) eluting with MeOH-H$_2$O (1:1) and collecting 2 mL fractions. The appropriate fractions were combined, evaporated, lyophilized, and pump-dried to give 12 (0.149 g, 78%) as a very hygroscopic white lyophilate: $^1$H-NMR (CD$_3$OD, 80 Mhz) δ1.59 (s, 9H, 3×CH$_3$), 1.64 (s, 6H, 2×CH$_3$), 2,00 (m, 14H, 7×CH$_2$), 2.31 (m, 2H, CH$_2$), 2.42 (dd, 2H, J=16.3, 20.8 Hz, PCH$_2$P), 5.11 (br, 4H, 4×CH), MS (FAB$^+$) m/e 561 (M+H)$^+$.

EXAMPLE 13

Synthesis of the tripotassium salt of (E,E,E)-1-methyl-1-[(4,8,12,16-tetramethyl-3,7,11,15-heptadecatetraenyl)hydroxyphosphoryl] ethylphosphonic aci.

Compound 13 was prepared as shown in SCHEME 11

SCHEME 11

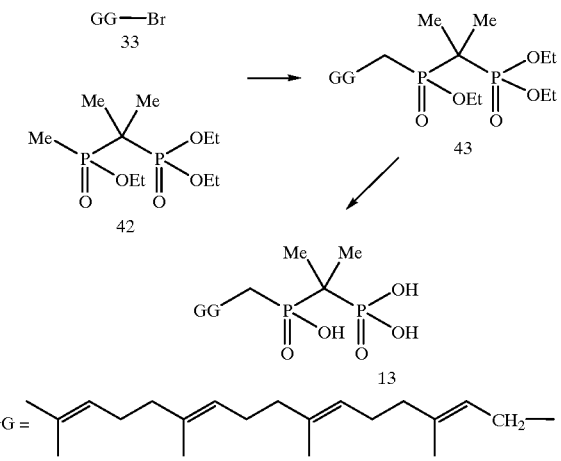

a) Synthesis of diethyl (E,E,E)-1-methyl-1-[(4,8,12,16-tetramethyl-3,7,11,15-heptadecatetraenyl) ethoxyphosphoryl]ethylphosphonate (43).

Butyllithium (0.56 ml, of 1.6 M hexane solution, 0.9 mmol) was added dropwise to a stirred solution of intermediate 42, diethyl 1-[ethoxy(methyl)phosphinoyl]-1-methylethylphosphonate, (0.200 g, 0.70 mmol), prepared as disclosed by M. Prashad, J. C. Tomesch, J. R. Wareing, T. Scallen, *Eur. J. Med. Chem*, 28, 527–531, 1993, in anhydrous THF (3 mL), cooled at −78° C. and under an argon atmospher. The resulting mixture, after stirring for 1 h at −78° C. was treated dropwise with intermediate 33 (0.353 g, 1.0 mmol) and then stirred for an additional 1 h at −78° C. The reaction mixture was quenched with acetic acid (0.120 g, 2 mmol), diluted with $CH_2Cl_2$ (15 mL) and washed with brine. The organic phase was dried and evaporated under reduced pressure. The residue was purified by column chromatography on 230–400 mesh silica gel (Macherey-Nagel Silica Gel 60 Art. Nr. 81538) eluting with hexane-AcOEt (1:3) and collecting 3 mL fractions. The appropriate fractions were combined, evaporated, and pump-dried to give intermediate 43 (0.210 g, 38%) as an oil: $^1$H-NMR (CDCl$_3$, 80 Mhz) δ1.35 (m, 15H, 2×CH$_3$+3×CH$_3$CH$_2$), 1.63 (s, 9H, 3×CH$_3$), 1.70 (s, 6H, 2×CH$_3$), 2.07 (m, 14H, 7×CH$_2$), 2.28 (m, 2H, CH$_2$), 4.18 (m, 6H, 3×CH$_3$CH$_2$), 5.12 (br, 4H, 4×CH); MS (FAB$^+$) m/e 559 (M+H)$^+$.

Synthesis of 13. Bromotrimethylsilane (0.152 mL, 1.15 mmol) was added to a stirred solution of compound 43 (0.128 g, 0.23 mmol) and 2,4,6-collidine (0.06 mL, 0.46 mmol) in anhydrous CH$_2$Cl$_2$ (6 mL); the resulting mixture was stirred at rt for 18 h. After evaporation of the solution, the residue was treated with an aqueous solution of KOH 1.0 N (1.7 mL) and then stirred at rt for 3 h. The solution was evaporated and the resulting crude residue was purified by column chromatography on reverse phase silica gel (Macherey-Nagel Polygosil® 60-4063 C$_{18}$ Art. Nr. 71150) eluting with MeOH—H$_2$O (3:4) and collecting 2 mL fractions. The appropriate fractions were combined, evaporated, lyophilized, and pump-dried to give 13 (0.115 g, 85%) as a very hygroscopic white lyophilate: $^1$H-NMR (CD$_3$OD, 80 MHz) δ1.18 (m, 6H, 2×CH$_3$), 1.59 (s, 9H, 3×CH$_3$), 1.65 (s, 6H, 2×CH$_3$), 2.03 (m, 14H, 7×CH$_2$), 5.15 (br, 4H, 4×CH); MS (FAB$^+$) m/e 589 (M+H)$^+$.

EXAMPLE 14

Synthesis of the tripotassium salt of (E,E,E)-1-ethyl-1-[(4,8,12,16-tetramethyl-3,7,11,15-heptadecatetraenyl)hydroxyphosphoryl]propylphosphonic acid.

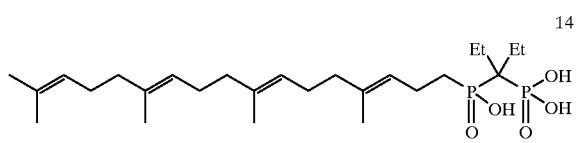

14

Compound 14 was prepared as shown in SCHEME 12

SCHEME 12

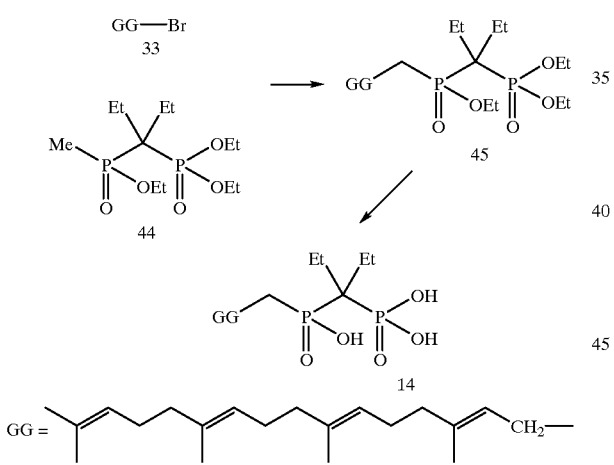

a) Synthesis of diethyl (E,E,E)-1-ethyl-1-[(4,8,12,16-tetramethyl-3,7,11,15-heptadecatetraenyl)ethoxyphosphoryl]propylphosphonate acid (45).

Butyllithium (0.63 mL, of 1.6 M hexane solution, 1.0 mmol) was added dropwise to a stirred solution of intermediate 44, diethyl 1-[ethoxy(methyl)phosphinoyl]-1-ethylpropylphosphonate, (0.260 g, 0.83 mmol, prepared as disclosed by M. Prashad, J. C. Tomesch, J. R. Wareing, T. Scallen, Eur. J. Med. Chem, 28, 527–531, 1993, in anhydrous THF (3 mL), cooled at −78° C. and under an argon atmosphere. The resulting mixture, after stirring for 1 h at −78° C. was treated dropwise with intermediate 33 (0.410 g, 1.16 mmol) and then stirred for an additional 1 h at −78° C. The reaction mixture was quenced with acetic acid (0.139 g, 2.32 mmol), diluted with CH$_2$Cl$_2$ (15 mL) and washed with brine. The organic phase was dried and evaporated under reduced pressure. The residue was purified by column chromatography on 230–400 mesh silica get (Macherey-Nagel Silica Gel 60 Art. Nr. 81538) eluting with hexane-AcOEt (1:3) and collecting 3 mL fractions. The appropriate fractions were combined, evaporated, and pump-dried to give intermediate 45 (0.219 g, 32%) as an oil: $^1$H-NMR (CDCl$_3$, 80 Mhz) δ1.19 (m, 15H, 5×CH$_3$CH$_2$), 1.55 (s, 12H, 4×CH$_3$), 1.63 (s, 3H, CH$_3$), 1.98 (m, 18H, 9×CH$_2$), 2.25 (m, 2H, CH$_2$), 4.10 (m, 6H, 3×CH$_3$CH$_2$), 5.14 (br, 4H, 4×CH); MS (FAB$^+$) m/e 587 (M+H)$^+$.

Synthesis of 14. Bromotrimethylsilane (0.178 mL, 1.35 mmol) was added to a stirred solution of compound 45 (0.160 g, 0.27 mmol) and 2,4,6-collidine (0.071 mL, 0.54 mmol) in anhydrous CH$_2$Cl$_2$ (6 mL); the resulting mixture was stirred at rt for 18 h. After evaporation of the solution, the residue was treated with an aqueous solution of KOH 1.0N (2.0 mL) and then stirred at rt for 3 h. The solution was evaported and the resulting crude residue was purified by column chromatography on reverse phase silica gel (Macherey-Nagel Polygosil® 60-4063 C$_{18}$ Art. Nr. 71150) eluting with MeOH-H$_2$O (3:4) and collecting 2 mL fractions. The appropriate fractions were combined, evaporated, lyophilized, and pump-dried to give 14 (0.149 g, 89%) as a very hygroscopic white lyophilate: $^1$H-NMR (CD$_3$OD, 80 Mhz) δ1.04 (m, 6H, 2×CH$_3$CH$_2$), 1.54 (s, 9H, 3×CH$_3$), 1.62 (s, 6H, 2×CH$_3$), 1.94 (m, 18H, 9×CH$_2$), 2.24 (m, 2H, CH$_2$), 5.12 (br, 4H, 4×CH); MS (FAB$^+$) m/e 617 (M+H)$^+$.

EXAMPLE 15

Synthesis of the tripotassium salt of (E,E,E)-[[(3,7,11,15-tetramethyl-2,6,10,14-hexadecatetraenyloxymethyl)hydroxyphosphoryl]methyl]phosphonic acid.

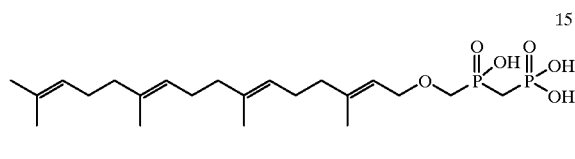

15

Compound 15 was prepared as shown in SCHEME 13

SCHEME 13

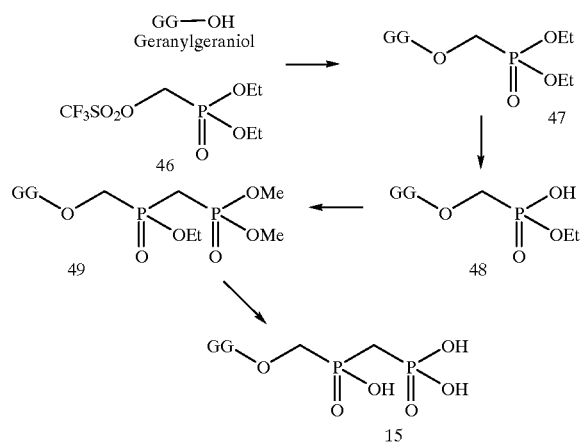

-continued

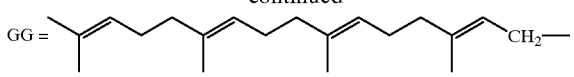

GG = a) Syntesis of diethyl (E,E,E)-(3,7,11,15-tetramethyl-2,6,10,14-hexadecatetraenyloxymethyl) phosphonate (47).

Butyllithium (2.1 mL of 1.6 M hexane solution, 3.36 mmol) was added dropwise over 10 min to a stirred solution of geranylgeraniol (1 g, 3.44 mmol) in anhydrous THF (12 mL), cooled at −78° C. and under an argon atmosphere. The mixture, after stirring for 1 h at −78° C., was treated dropwise with a solution of intermediate 46, diethyl phosphonomethyltriflate, (0.94 g, 3.13 mmol, prepared as disclosed by D. P. Phillion, S. S. Andrew, *Tetrahedron Letters*, 27, 1477–1480, 1986, in anhydrous THF (3 mL). The mixture was stirred for 1 h at −78° C. and then allowed to warm to 0° C. for 2 h. The reaction mixture was quenched with a saturated aqueous ammonium chloride solution and extracted with Et$_2$O. The organic phase was dried and evaporated under reduced pressure. The resulting residue was purified by column chromatography on 230–400 mesh silica get (Macherey-Nagel Silica Gel 60 Art. Nr. 81538) eluting with hexane-AcOEt (3:1) and collecting 4 mL fractions. The appropriate fractions were combined, evaporated, and pump-dried to give intermediate 47 (0.771 g, 51%) as an oil: $^1$H-NMR (CDCl$_3$, 80 Mhz) 1.34 (t, 6H, J=7.2 Hz, 2×CH$_3$CH$_2$), 1.59 (s, 9H, 3×CH$_3$), 1.67 (s, 6H, 2×CH$_3$), 2.02 (m, 12H, 6×CH$_2$), 3.71 (d, 2H, J=8.8 Hz, CH$_2$), 4.10 (m, 6H, CH$_2$+2×CH$_3$CH$_2$), 5.08 (br, 3H, 3×CH), 5.30 (t, 1H, J=7.2 Hz, CH); MS (FAB$^+$) m/e 441 (M+H)$^+$.

b) Synthesis of ethyl (E,E,E)-(3,7,11,15-tetramethyl-2,6,10,14-hexadecatetraenyloxymethyl) phosphonate (48).

A solution of intermediate 47 (0.626 g, 1.42 mmol) in 2-propanol (10 mL) was treated with KOH 1N (12 mL) and the resulting mixture was stirred at 110° C. for 48 h. The 2-propanol was evaporated and the aqueous residue was acidified with 10% aqueous HCl and then extracted with CH$_2$Cl$_2$ (3×20 mL), the organic phase was washed with brine, dried and evaporated to give 48 (0.550 g, 94%) as an oil: $^1$H-NMR (CDCl$_3$, 80 Mhz) 1.33 (t, 3H, J=7.2 Hz, CH$_3$CH$_2$), 1.59 (s, 9H, 3×CH$_3$), 1.66 (s, 6H, 2×CH$_3$), 2.02 (m, 12H, 6×CH$_2$), 3.70 (d, 2H, J=8.8 Hz, CH$_2$), 4.11 (m, 4H, CH$_2$+CH$_3$CH$_2$), 5.08 (br, 3H, 3×CH), 5.29 (t, 1H, J=7.2 Hz, CH); MS (FAB$^+$) m/e 413 (M+H)$^+$.

Synthesis of dimethyl (E,E,E)-[[(3,7,11,15-tetramethyl-2,6,10,14-hexadecatetraenyloxymethyl)ethoxyphosphoryl]methyl]phosphonate (49). N,N-diethyl(trimethylsilyl)amine (0.33 mL, 1.73 mmol) was added to a stirred solution of intermediate 48 (0.360 g, 0.87 mmol) in anhydrous CH$_2$Cl$_2$ (6 mL), under an argon atmosphere, and the resulting mixture was stirred for 2 h at room temperature. The solvent was evaporated and the residue was dissolved in benzene, evaporated and then pumped at high vacuum. The remainder was dissolved, under an argon atmosphere, in anhydrous CH$_2$Cl$_2$ (6 mL) containing three drops of anyhdrous DMF and the resulting solution was then treated dropwise, at 0° C. and under an argon atmosphere, with freshly distilled oxalyl chloride (0.16 mL, 1.8 mmol) with much gas evolution. The reaction mixture was stirred for 1 h at 0° C. and then allowed to warm to room temperature for 1 h. The solution was evaporated and the residue was twice dissolved in anhydrous benzene and evaporated under reduced pressure to give the resulting acid chloride. Buthyllithium (1.2 mL of 1.6M hexane solution, 1.92 mmol) was added dropwise over 5 min to a stirred solution of dimethylmethylphosphonate (0.21 mL, 2 mmol), cooled at −78° C. and under an argon atmosphere, and the resulting mixture was stirred at −78° C. for 1 h. The resulting suspension at −78° C. and under an argon atmosphere was treated dropwise over 10 min with an anhydrous THF (4 mL) solution of the acid chloride prepared above. The reaction mixture was stirred at −78° C. for 1 h, quenched with a saturated aqueous ammonium chloride solution and diluted with Et$_2$O. The aqueous layer was acidified with 10% aqueous HCl and the organic phase was separated and washed with brine. The aqueous layer was re-extracted with CH$_2$Cl$_2$, and the CH$_2$Cl$_2$ washed with brine. The combined organic layers were dried and evaporated. The residue was purified by column chromatography on 230–400 mesh silica get (Macherey-Nagel Silica Gel 60 Art. Nr. 81538) eluting with MeOH-CH$_2$Cl$_2$ (2:98) and collecting 3 mL. fractions. The appropriate fractions were combined, evaporated, and pump-dried to give intermediate 49 (0.320 g, 71%) as an oil: $^1$H-NMR (CDCl$_3$, 80 Mhz) δ1.34 (t, 3H, J=7.2 Hz, CH$_3$CH$_2$), 1.59 (s, 9H, 3×CH$_3$), 1.67 (s, 6H, 2×CH$_3$), 2.03 (m, 12H, 6×CH$_2$), 2.55 (m, 2H, CH$_2$), 3.75 (m, 2H, CH$_2$), 3.80 (d, 3H, J=6 Hz, CH$_3$), 3.84 (d, 3H, J=6 Hz, CH$_3$), 4.10 (m, 4H, CH$_2$+CH$_3$CH$_2$), 5.09 (br, 3H, 3×CH), 5.30 (t, 1H, J=7.2 Hz, CH); MS (FAB$^+$) m/e 519 (M+H)$^+$.

Synthesis of 15. Bromotrimethylsilane (0.356 mL, 2.7 mmol) was added to stirred solution of compound 49 (0.280 g, 0.54 mmol) and 2,4,6-collidine (0.143 mL, 1.08 mmol) in anhydrous CH$_2$Cl$_2$ (8 mL); the resulting mixture was stirred at rt for 18 h. After evaporation of the solution, the residue was treated with an aqueous solution of KOH 1.0N (4.1 mL) and then stirred at rt for 3 h. The solution was evaporated and the resulting crude residue was purified by column chromatography on reverse phase silica get (Macherey-Nagel Polygosil® 60-4063 C$_{18}$ Art. Nr. 71150) eluting with MeOH-H$_2$O (3:4) and collecting 2 mL fractions. The appropriate fractions were combined, evaporated, lyophilized, and pump-dried to give 15 (0.186 g, 60%) as a very hygroscopic white lyophilate: $^1$H-NMR (CD$_3$OD, 80 Mhz) δ1.59 (s, 9H, 3×CH$_3$), 1.67 (s, 6H, 2×CH$_3$), 2.02 (m, 14H, 7×CH$_2$), 3.59 (d, 2H, J=6.5 Hz, CH$_2$), 4.06 (d, 2H, J=7.2 Hz, CH$_2$), 5.09 (br, 3H, 3×CH), 5.30 (t, 1H, J=7.2 Hz, CH); MS (FAB$^+$) m/e 577 (M+H)$^+$.

EXAMPLE 16

Synthesis of the dipotassium salt of (E,E,E)-(4,8,12,16-tetramethyl-3,7,11,15-heptadecatetraenyl) phosphonic acid.

16

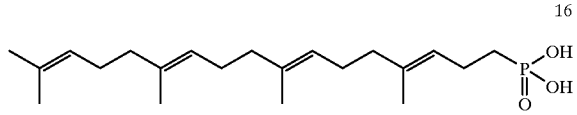

Compound 16 was prepared as shown in SCHEME 14

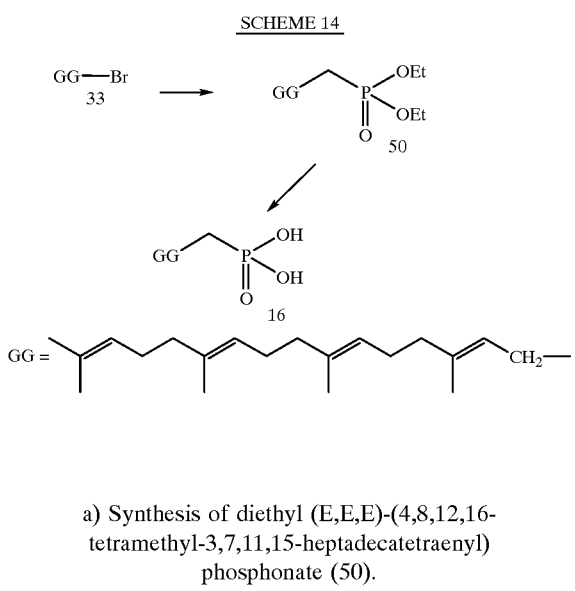

a) Synthesis of diethyl (E,E,E)-(4,8,12,16-tetramethyl-3,7,11,15-heptadecatetraenyl) phosphonate (50).

Butyllithium (0.48 mL of 1.6M hexane solution, 0.76 mmol) was added dropwise to a stirred solution of diethylmethylphosphonate (0.086 mL, 0.59 mmol) in anhydrous THF (3 mL), cooled at −78° C. and under an argon atmosphere. The resulting mixture, after stirring for 1 h at −78° C. was treated dropwise with intermediate 33 (0.300 g, 0.85 mmol) and then stirred for an additional 1 h at −78° C. The reaction mixture was quenched with acetic acid (0.102 g, 1.7 mmol), diluted with $CH_2Cl_2$ (15 mL) and washed with brine. The organic phase was dried and evaporated under reduced pressure. The residue was purified by column chromatography on 230–400 mesh silica gel (Macherey-Nagel Silica Gel 60 Art. Nr. 81538) eluting with hexane-AcOEt (7:3) and collecting 3 mL fractions. The appropriate fractions were combined, evaporated, and pump-dried to give intermediate 50 (0.188 g, 75%) as an oil: $^1$H-NMR (CDCl$_3$, 80 Mhz) 1.31 (t, 6H, J=7.2 Hz, 2×CH$_3$CH$_2$), 1.59 (s, 9H, 3×CH$_3$), 1.67 (s, 3H, CH$_3$), 1.71 (s, 3H, CH$_3$), 1.99 (m, 14H, 7×CH$_2$), 2.29 (m, 2H, CH$_2$), 4.07 (m, 4H, 2×CH$_2$CH$_2$), 5.08 (br, 4H, 4×CH); MS (FAB$^+$) m/e 425 (M+H)$^+$.

Synthesis of 16. Bromotrimethylsilane (0.165 ml, 1.25 mmol) was added to a stirred solution of compound 50 (0.106 g, 0.25 mmol) and 2,4,6-collidine (0.066 mL, 0.50 mmol) in anhydrous CH$_2$Cl$_2$ (6 mL); the resulting mixture was stirred at rt for 18 h. After evaporation of the solution, the residue was treated with an aqueous solution of KOH 1.0 N (1.9 mL) and then stirred at rt for 3 h. The solution was evaporated and the resulting crude residue was purified by column chromatography on reverse phase silica gel (Macherey-Nagel Polygosil 60-4063 C$_{18}$ Art. Nr. 71150) eluting with MeOH—H$_2$O (1:2) and collecting 2 ml. fractions. The appropriate fractions were combined, evaporated, lyophilized, and pump-dried to give 16 (0.100 g, 90%) as a very hygroscopic white lyophilized: $^1$H-NMR (CD$_3$OD, 80 Mhz) 1.59 (s, 9H, 3×CH$_3$), 1.64 (s, 3H, CH$_3$), 1.67 (s, 3H, CH$_3$), 2.02 (m, 14H, 7×CH$_2$), 2.22 (m, 2H, CH$_2$), 5.14 (br, 4H, 4×CH); MS (FAB$^+$) m/e 445 (M+H)$^+$.

EXAMPLE 17

Synthesis of Dipotassium Salt of (E,E,E)-(1-hydroxy-3,7,11,15-tetramethyl-2,6,10,14-hexadecatetraenyl)phosphonic Acid

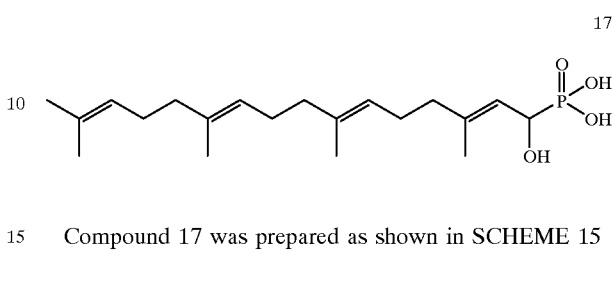

Compound 17 was prepared as shown in SCHEME 15

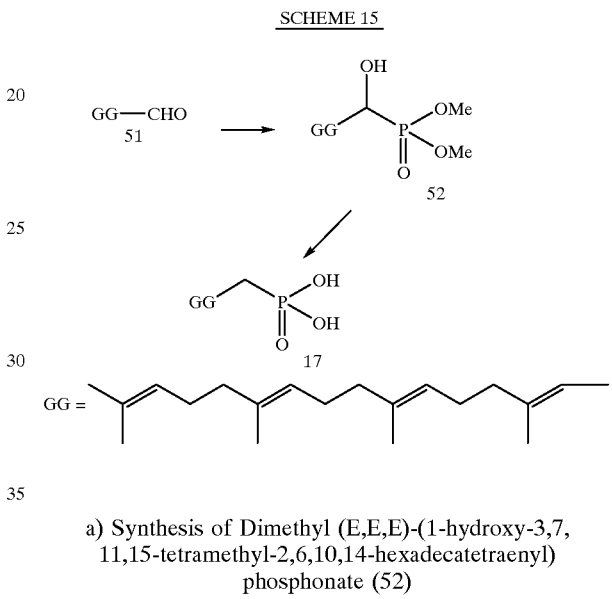

a) Synthesis of Dimethyl (E,E,E)-(1-hydroxy-3,7,11,15-tetramethyl-2,6,10,14-hexadecatetraenyl) phosphonate (52)

Dimethylphosphite (0.18 mL, 1.96 mmol) and triethylamine (0.36 ml, 2.6 mmol) were added to a stirred solution of geranygeranial (51, 0.374 g, 1.3 mmol, prepared as disclosed by A. J. Mancuso, S. I. Huang, D. Swern. *J. Org. Chem.*, 43, 2480, 1978, in anhydrous CH$_3$CN (3 mL) under an argon atmosphere. The mixture was stirred at rt for 24 h, and the solvent was evaporated under reduced pressure. The residue was purified by column chromatography on 230–400 mesh silica gel (Macherey-Nagel Silica Gel 60 Art. Nr. 81538) eluting with AcOEt-hexane (1:1.5) and collecting 3 ml. fractions. The appropriate fractions were combined, evaporated, and pump-dried to give intermediate 52 (0.160 g, 31%) as an oil; MS (FAB$^+$) m/e 399 (M+H)$^+$.

Synthesis of 17. Bromotrimethylsilane (0.25 ml., 1.88 mmol) was added to a stirred solution of compound 52 (0.150 g, 0.377 mmol) and 2,4,6-collidine (0.10 mL, 0.754 mmol) in anhydrous CH$_2$Cl$_2$ (5 mL); the resulting mixture was stirred at rt for 18 h. After evaporation of the solution, the residue was treated with an aqueous solution of KOH 1.0 N (2.9 mL) and then stirred at rt for 3 h. The solution was evaporated and the resulting crude residue was purified by column chromatography on reverse phase silica gel (Macherey-Nagel Polygosil 60-4063 C$_{18}$ Art. Nr. 71150) eluting with MeOH—H$_2$O (1:2) and collecting 2 mL fractions. The appropriate fractions were combined, evaporated, lyophilized, and pump-dried to give 17 (0.070 g, 42%) as a very hygroscopic white lyophilate: MS (FAB$^+$) m/e 447 (M+H)$^+$.

EXAMPLE 18

Synthesis of (E,E,E)-O-(3,7,11,15-tetramethyl-2,6,10,14-hexadecatetraenyl)-N-(aminosulfonyl)urethane

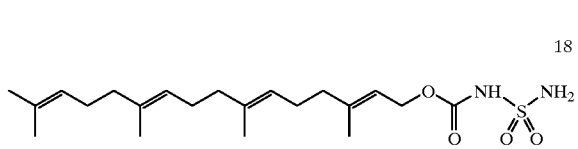

A solution of geranylgeraniol (0.5 g, 1.72 mmol) in anhydrous CH$_3$CN (15 mL) at −20° C. under nitrogen was treated with chlorosulfonylisocyanate (0.15 ml., 1.72 mmol) and the mixture was stirred at −20° C. for 4 h. The mixture was then treated dropwise at −20° C. with a saturated solution of NH$_3$ in CH$_3$CN (7 mL) and left at −20° C. for 3 h under stirring. The solvent was evaporated under reduced pressure and the residue was purified by column chromatography on reverse phase silica gel (Macherey-Nagel Polygosil 60-4063 C$_{18}$ Art. Nr. 71150) eluting with CH$_2$CN—H$_2$O (6:4) and collecting 6 ml. fractions. The appropriate fractions were combined, evaporated, lyophilized, and pump-dried to give 18 (0.4 g, 56%) as a very hygroscopic white lyophiliate: $^1$H-NMR (CDCl$_3$, 80 Mhz) δ 1.60 (s, 9H, 3×CH$_3$), 1.68 (s, 3H, CH$_3$), 1.71 (s, 3H, CH$_3$), 2.03 (m, 12H, 6×CH$_2$), 4.30 (br, 3H, D$_2$O exchangeable, NH+NH$_2$), 4.68 (d, 2H, J=7.2 Hz, CH$_2$), 5.10 (br, 3H, 3×CH), 5.38 (t, 1H, J=7.2 Hz, CH); MS (FAB$^-$) m/e 411 (M—H)$^-$.

EXAMPLE 19

Synthesis of (E,E,E)-1-1(aminosulfonyl)aminoxyl-3,7,11,15-tetramethyl-2,6,10,14-hexadecatetraene

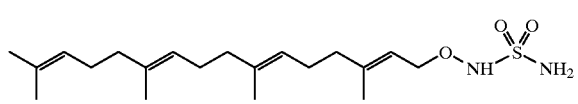

A mixture of sulfamoyl chloride (0.147 g, 1.28 mmol, prepared as disclosed by R. Appel, G. Berger, *Chem. Ber.*, 91, 1339, 1958, and K$_2$CO$_3$ (1 g, 7.2 mmol) in anhydrous dioxane (12 ml) was treated with intermediate 21 (0.300 g, 0.98 mmol) and the resulting mixture was stirred for 36 h at room temperature. The reaction mixture was filtered and evaporated. The residue was purified by column chromatography on 230–400 mesh silica gel (Macherey-Nagel Silica Gel 60 Art. Nr. 81538) eluting with hexane-AcOEt (4:1) and collecting 3 mL fractions. The appropriate fractions were combined, evaporated, and pump-dried to give 19 (0.327 g, 87%) as a very hygroscopic white solid: $^1$H-NMR (CDCl$_3$, 80 Mhz) δ 1.60 (s, 9H, 3×CH$_3$), 1.68 (s, 3H, CH$_3$), 1.72 (s, 3H, CH$_3$), 2.04 (m, 12H, 6×CH$_2$), 4.28 (br, 3H, D$_2$O exchangeable, NH+NH$_2$), 4.51 (d, 2H, J=7.2 Hz, CH$_2$), 5.10 (br, 3H, 3×CH), 5.37 (t, 1H, J=7.2 Hz, CH); MS (FAB$^+$) m/e 385 (M—H)$^+$.

What is claimed is:
1. A compound of formula:

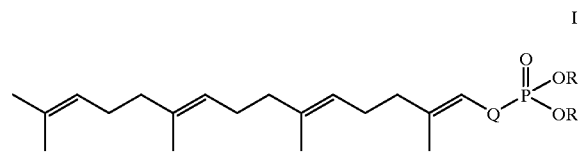

wherein:

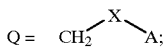

X=ONH, ONHCO, OCH$_2$CO, OCH$_2$P(O)OH, CH$_2$P(O)OH, OSO$_2$, NHSO$_2$;
A=R'CR", CHR'"CH$_2$, NH when X=OSO$_2$, NHSO$_2$;
R=H, CH$_3$, CH$_2$CH$_3$;
R'=H, CH$_3$, CH$_2$CH$_3$;
R"=H, CH$_3$, CH$_2$CH$_3$;
R'"=H, COOH, COOEt, COOMe;
and pharmaceutically acceptable salts thereof, with organic and inorganic acids or bases.

2. (E,E,E)-{2-oxo-2-[[(3,7,11,15-tetramethyl-2,6,10,14-hexadecatetraenyl)oxy]amino]ethyl}phosphonic acid and pharmaceutically acceptable salts thereof, with organic and inorganic acids or bases.

3. Ethyl-(E,E,E)-{2-oxo-2-[[(3,7,11,15-tetramethyl-2,6,10,14-hexadecatetraenyl)oxy]amino]ethyl}phosphonate and pharmaceutically acceptable salts thereof, with organic and inorganic acids or bases.

4. (E,E,E)-1[[(3,7,11,15-tetramethyl-2,6,10,14-hexadecatetraenyl)oxy]aminocarbonyl]ethylphosphonic acid and pharmaceutically acceptable salts thereof, with organic and inorganic acids or bases.

5. (E,E,E)-1-[[(3,7,11,15-tetramethyl-2,6,10,14-hexadecatetraenyl)oxy]aminocarbonyl]propylphosphonic acid and pharmaceutically acceptable salts thereof, with organic and inorganic acids or bases.

6. (E,E,E)-{3-oxo-3-[[(3,7,11,15-tetramethyl-2,6,10,14-hexadecatetraenyl)oxy]amino]propyl}phosphonic acid and pharmaceutically acceptable salts thereof, with organic and inorganic acids or bases.

7. (E,E,E)-3-oxo-2-(phosphonomethyl)-3-[[(3,7,11,15-tetramethyl-2,6,10,14-hexadecatetraenyl)oxy]amino]propyl}propanoic acid and pharmaceutically acceptable salts thereof, with organic and inorganic acids or bases.

8. (E,E,E)-[[(4,8,12,16-tetramethyl-3,7,11,15-hexadecatetraenyl)hydroxyphosphoryl]methyl]phosphonic acid and pharmaceutically acceptable salts thereof, with organic and inorganic acids or bases.

9. (E,E,E)-1-methyl-1-[(4,8,12,16,tetramethyl-3,7,11,15-heptadecatetraenyl)hydroxyphosphoryl]ethylphosphonic acid and pharmaceutically acceptable salts thereof, with organic and inorganic acids or bases.

10. (E,E,E)-1-ethyl-1-[(4,8,12,16-tetramethyl-3,7,11,15-heptadecatetraenyl)hydroxyphosphoryl]propylphosphonic acid and pharmaceutically acceptable salts thereof, with organic and inorganic acids or bases.

11. (E,E,E)-[[(3,7,11,15-tetramethyl-2,6,10,14-hexadecatetraenyloxymethyl)hydroxyphosphoryl]methyl]phosphonic acid and pharmaceutically acceptable salts thereof, with organic and inorganic acids or bases.

12. Diethyl (E,E,E)-{2-oxo-2-[[(3,7,11,15-tetramethyl-2,6,10,14-hexadecatetraenyl)oxy]amino]ethyl}phosphonate.

13. Diethyl (E,E,E)-1-[[(3,7,11,15-tetramethyl-2,6,10,14-hexadecatetraenyl)oxy]amino-carbonyl]ethylphosphonate.

14. Diethyl (E,E,E)-1-[[(3,7,11,15-tetramethyl-2,6,10,14-hexadecatetraenyl)oxy]amino-carbonyl]propylphosphonate.

15. Diethyl (E,E,E)-{3-oxo-3-[[(3,7,11,15-tetramethyl-2,6,10,14-hexadecatetraenyl)oxy]amino]propyl}phosphonate.

16. Ethyl (E,E,E)-3-oxo-2-(diethylphosphonomethyl)-3-[[(3,7,11,15-tetramethyl-2,6,10,14-hexadecatetraenyl)oxy]amino]phosphonate.

17. Diethyl (E,E,E)-[[4,8,12,16-tetramethyl-3,7,11,15-heptadecatetraenyl)ethoxyphosphoryl]methyl]phosphonate.

18. Diethyl (E,E,E)-1-methyl-1-[4,8,12,16-tetramethyl-3,7,11,15-heptadecatetraenylethoxyphosphoryl]ethylphosphonate.

19. Diethyl (E,E,E)-1-ethyl-1-[(4,8,12,16-tetramethyl-3,7,11,15-heptadecatetraenyl)ethoxyphosphoryl]propylphosphonate acid.

20. Dimethyl (E,E,E)-[[3,7,11,15-tetramethyl-2,6,10,14-hexadecatetraenyloxymethyl)ethoxyphosphoryl]methyl]phosphonate.

21. A compound of formula:

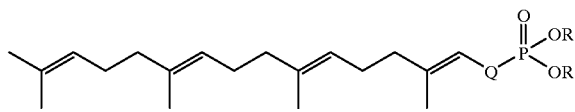

wherein:

Q=

A=R'CR", CHR'"CH$_2$,
R=H, CH$_3$, CH$_2$CH$_3$,
R'=H, CH$_3$, CH$_2$CH$_3$;
R"=CH$_3$;
R'"=COOH, COOEt, COOMe;
and pharmaceutically acceptable salts thereof, with organic and inorganic acids or bases.

22. (E,E,E)-1-[[(3,7,11,15-tetramethyl-2,6,10,14-hexadecatetraenyl)aminocarbonyl]propylphosphonate acid and pharmaceutically acceptable salts thereof, with organic and inorganic acids or bases.

23. (E,E,E)-3-oxo-2-(phosphonomethyl)-3-[(3,7,11,15-tetramethyl-2,6,10,14-hexadecatetraenyl)amino]propanoic acid and pharmaceutically acceptable salts thereof, with organic and inorganic acids or bases.

24. Diethyl (E,E,E)-1-[(3,7,11,15-tetramethyl-2,6,10,14-hexadecatetraenyl)aminocarbonyl]propylphosphonate.

25. A pharmaceutical composition comprising a compound according to claim 1 as active principle.

26. A pharmaceutical composition comprising a compound according to claim 21 as active principle.

27. A pharmaceutical composition comprising a compound according to claim 22 as active principle.

28. A pharmaceutical composition comprising a compound according to claim 23 as active principle.

29. A pharmaceutical composition comprising a compound according to claim 24 as active principle.

* * * * *